(12) United States Patent
Brinkmann et al.

(10) Patent No.: US 8,747,834 B2
(45) Date of Patent: Jun. 10, 2014

(54) METHODS OF TREATING IMPAIRED GLUCOSE METABOLISM VIA ADMINISTRATION OF ALGAL BIOMASS

(75) Inventors: David Brinkmann, South San Francisco, CA (US); Anthony G. Day, San Francicso, CA (US); Peter J. H. Jones, Winnipeg (CA); Scott Harding, Winnipeg (CA)

(73) Assignees: Solazyme, Inc., South San Francisco, CA (US); University of Manitoba, Winnipeg (CA)

( * ) Notice: Subject to any disclaimer, the term of this patent is extended or adjusted under 35 U.S.C. 154(b) by 255 days.

(21) Appl. No.: 13/254,035

(22) PCT Filed: Mar. 3, 2010

(86) PCT No.: PCT/US2010/026117
§ 371 (c)(1),
(2), (4) Date: Sep. 27, 2011

(87) PCT Pub. No.: WO2010/102056
PCT Pub. Date: Sep. 10, 2010

(65) Prior Publication Data
US 2012/0027724 A1 Feb. 2, 2012

Related U.S. Application Data

(60) Provisional application No. 61/157,170, filed on Mar. 3, 2009.

(51) Int. Cl.
*A01N 63/00* (2006.01)
*A01N 65/00* (2009.01)

(52) U.S. Cl.
USPC ....................................................... 424/93.1

(58) Field of Classification Search
None
See application file for complete search history.

(56) References Cited

U.S. PATENT DOCUMENTS

| | | |
|---|---|---|
| 2005/0008656 A1 | 1/2005 | Meredith |
| 2008/0019997 A1 | 1/2008 | Shaish et al. |
| 2009/0047721 A1 | 2/2009 | Trimbur et al. |

OTHER PUBLICATIONS

Xu et al., Journal of Biotechnology, 2006, vol. 126, p. 499-507.*
Parikh et al., Journal of Medicinal Food, 2001, vol. 4, No. 4, p. 193-199.*
Ötles & Pire, Journal of AOAC International, 2001, vol. 84, No. 6, p. 1708-1714.*
Cherng et al., Life Sciences, 2006, vol. 78, No. 1181-1186.*
Hidaka et al., Phytotherapy Research, 2004, vol. 18, p. 164-168.*
Curtain, "Plant Biotechnology—The growth of Australia's algal b-carotene industry," *Australasian Biotechnology*, 10(3):18-23, (2000). [Retrieved from the Internet on Apr. 5, 2010 <URL:http://www.bioline.org.barequest?au00032>].
GenBank Accesssion No. L42851, "Prototheca wickerhamii large subunit ribosomal RNA (rrnL) gene, partial sequence; chloroplast gene for chloroplast product," (2001). [Retrieved from the Internet retrieved on Apr. 4, 2010 <URL:http://www.ncbi.nlm.nih.gov/nuccore/17028073>].
GenBank Accession No. L43357, "Chlorella vulgaris chloroplast large subunit ribosomal RNA (rmL) gene," (2005). [Retrieved from the Internet on Apr. 4, 2010 <URL:http://www.ncbi.nlm.nih.gov/nuccore/17028301>].
Jong-Yuh et al., "Potential hypoglycemic effects of Chlorella in streptozotocin-induced diabetic mice," *Life Sciences*, 77:980-990, (2005).
Mizoguchi et al., "Nutrigenomic Studies of Effects of Chlorella on Subjects with High-Risk Factors for Lifestyle-Related Disease," *Journal of Medicinal Food*, 11(3):395-404, (2008).
PCT Search Report for application PCT/US2010/026117 mailed May 27, 2010.
PCT Written Opinion of the International Searching Authority for application PCT/US2010/026117 mailed May 27, 2010.
Rodriguez-Lopez et al., "Plasma-glucose and plasma-insulin in normal and alloxanized rats treated with Chlorella," *Life Sciences*, Part II, 10:57-60, (1971).
Sanchez et al., "Mixotrophic culture of Chlorella pyrenoidosa with olive-mill wastewater as the nutrient medium," *Journal of Applied Phycology*, 13:443-449, (2001).

\* cited by examiner

*Primary Examiner* — Kade Ariani
(74) *Attorney, Agent, or Firm* — Alston & Bird LLP

(57) ABSTRACT

The invention is directed to methods of using *Chlorella protothecoides* microalgal biomass in the treatment of individuals having impaired glucose metabolism. In some cases, the patient has impaired fasting glucose, impaired glucose tolerance, or diabetes. In some methods, algal biomass is used to reduce blood glucose and/or body fat in a subject, or to increase the relative abundance of beneficial gut microflora in a subject. In preferred embodiments, the biomass is derived from *Chlorella protothecoides* cultures grown heterotrophically in which the algal cells comprise at least 15% algal oil by dry weight.

17 Claims, 9 Drawing Sheets

METHODS OF TREATING IMPAIRED GLUCOSE METABOLISM VIA ADMINISTRATION OF ALGAL BIOMASS

REFERENCE TO A SEQUENCE LISTING

This application includes a sequence listing in a text file entitled 026172-004010PC_Seq_Listing.txt, created on Mar. 1, 2010, and containing 2918 bytes. The material contained in the text file is hereby incorporated by reference.

FIELD OF THE INVENTION

The invention resides in the fields of medicine, aquaculture, fermentation, and genetic engineering.

BACKGROUND OF THE INVENTION

Impaired glucose tolerance is a pre-diabetic state of dysglycemia, associated with insulin resistance and increased risk of cardiovascular disease and death. Barr et al., *Circulation* 116(2):151-157 (2007). In many cases, impaired glucose tolerance precedes the onset of type 2 diabetes, a disease characterized by insulin resistance, relative insulin deficiency, and hyperglycemia. Id.

Hyperglycemia is consistently associated with cardiovascular disease. Mazzone et al., *Lancet* 371:1800-1809 (2008). High blood glucose levels can lead to vascular complications by several mechanisms, resulting in atherosclerosis, among other complications. Id. As the incidence of obesity and type 2 diabetes continue to rise throughout many parts of the world, effective methods for combating the deleterious effects of hyperglycemia and preventing its occurrence are the focus of extensive research.

SUMMARY OF THE INVENTION

In one aspect, the present invention is directed to a method of treating a patient having impaired glucose metabolism by administering to the patient an effective treatment regime of *Chlorella protothecoides* biomass comprising at least 15% oil by dry weight. In some cases, the biomass contains at least 25%, 50% or 60% oil by dry weight. In some cases, the biomass contains 15-90%, 25-75%, 40-75% or 50-70% of algal oil by dry weight. In various embodiments, the patient, prior to being placed on the regimen, has been diagnosed with one or more conditions selected from the group consisting of impaired glucose tolerance, dysglycemia, insulin resistance, cardiovascular disease, diabetes (including but not limited to types 1, 1.5, 2, and 3), metabolic syndrome, hyperglycemia, and insulin deficiency.

In some embodiments, *Chlorella protothecoides* biomass used in the methods of the invention comprises oil in which at least 50% by weight of the oil is monounsaturated oil. In some cases, at least 50% by weight of the algal oil is oleic acid. In some cases, less than 5% by weight of the oil is docosahexanoic acid (DHA). In some embodiments, less than 1% by weight of the oil is DHA. In some cases, the oil is predominantly encapsulated in cells of the *Chlorella protothecoides* biomass.

In some embodiments, the patient treated via the administration of an effective regime of *Chlorella protothecoides* biomass is a patient having impaired glucose tolerance. In some cases, the patient has an impaired fasting glucose. In some embodiments, the patient has type 2 diabetes. In other cases, the patient has type 1 diabetes. In some cases, the patient has type 1.5 (type 3) diabetes.

In some embodiments of the present invention, the patient receives an alternative treatment, e.g., for impaired glucose tolerance, dysglycemia, insulin resistance, cardiovascular disease, diabetes (including but not limited to types 1, 1.5, 2, and 3), metabolic syndrome, hyperglycemia, and/or insulin deficiency, before the administering step and the alternative treatment is reduced or eliminated after the administering step. In some cases, the alternative treatment is administration of a non-algal pharmaceutical product.

In some methods in accordance with the present invention, the *Chlorella protothecoides* biomass regime lowers the mean plasma glucose concentration of the patient relative to the concentration before the administering step. In some cases, the mean plasma glucose concentration is lowered 10-50%. In some embodiments, the methods of the present invention further comprise monitoring blood glucose levels of the patient.

In some embodiments, the algal biomass regime lowers the percentage fat of total body weight in the patient relative to the percentage before the administering step.

In various embodiments, the algal biomass used in the methods of the present invention is derived from *Chlorella protothecoides* cultured and dried under good manufacturing practice (GMP) conditions. In some cases, the biomass is administered in the form of a tablet or capsule. In other cases, the biomass is administered in the form of a food product. In some embodiments, the food product comprises at least 50% algal biomass by weight.

In one aspect, the present invention is directed to a method of reducing blood glucose in a subject by administering to the subject an effective regime of *Chlorella protothecoides* biomass comprising at least 15% oil by dry weight, whereby the mean blood glucose level of the subject is reduced relative to the level before administering the regime. In some embodiments, the method further comprises monitoring the blood glucose level of the subject prior to administering the regime to detect the condition in need of treatment and then at various times after the regime is administered to detect the reduction. In various embodiments, the composition of the biomass or oil can be as described above, or throughout the specification.

In one aspect, the present invention is directed to a method of reducing body fat in a subject by administering to the subject an effective regime of *Chlorella protothecoides* biomass comprising at least 15% oil by dry weight, whereby the percentage fat of total body weight of the subject is reduced relative to the percentage fat of total body weight before administering the regime. In some cases, the subject has a body mass index of greater than 24.9. In some cases, the subject has a body mass index of greater than 29.9. In some embodiments, the method further comprises monitoring the percentage fat of total body weight in the subject prior to administering the regime to detect the condition in need of treatment and then at various times after the regime is administered to detect the reduction. In various embodiments, the composition of the biomass or oil can be as described above, or throughout the specification.

In one aspect, the present invention is directed to a method of increasing the relative abundance of beneficial gut microflora in a subject by administering to the subject an effective regime of *Chlorella protothecoides* biomass comprising at least 15% oil by dry weight, whereby the relative abundance of beneficial gut microflora is increased as compared to the relative abundance before administering the regime. In some cases, the beneficial gut microflora are of the class Lactobacillales. In some embodiments, the method further comprises monitoring the relative abundance of gut microflora in the subject prior to administering the regime to detect the condition in need of treatment and then at various times after the regime is administered to detect the increase. In various embodiments, the composition of the biomass or oil can be as described above, or throughout the specification.

In any one of the methods described above, the *Chlorella protothecoides* biomass regime can comprise administering the biomass at a dose of 1-20% of food by weight or calories. In some embodiments, the biomass is administered daily for at least a week, a month, a year, or for life. In some cases, the biomass is administered three times daily. In some cases, the algal biomass is administered proximate in time to intake of a meal. In some embodiments, the algal biomass is administered with at least one other edible ingredient as a food composition.

In any one of the methods described above, the biomass can be derived from a culture of the microalgae *Chlorella protothecoides*, including any strain of *Chlorella protothecoides* such as UTEX 1806, UTEX 411, UTEX 264, UTEX 256, UTEX 255, UTEX 250, UTEX 249, UTEX 31, UTEX 29, UTEX 25, CCAP 211/17 and CCAP 211/8d. *Chlorella protothecoides* strains have the 23S rRNA sequence of SEQ ID NOs: 5 or 6.

In any one of the methods described above, the microalgae can be grown heterotrophically. In some cases, microalgae are grown in a culture medium containing depolymerized cellulosic material. In some cases, the microalgae are grown in a culture medium containing a feedstock comprising at least one carbon substrate selected from the group consisting of cellulosic material, a 5-carbon sugar, and a 6-carbon sugar. In various embodiments, the carbon substrate can be selected from the group consisting of glucose, xylose, sucrose, fructose, arabinose, mannose, galactose, and any combination thereof.

In any one of the methods described above in which the at least one carbon substrate includes sucrose, the culture medium can optionally further include at least one sucrose utilization enzyme. In some cases, the at least one sucrose utilization enzyme is an exogenous enzyme introduced into the culture medium.

Some methods include first determining whether a patient or subject has a condition, is in need of treatment, or would otherwise benefit from administration of the compositions discussed herein. For example, some methods include first determining whether a patient or subject has impaired glucose metabolism, is in need of treatment to reduce body fat, or would benefit from a greater abundance of beneficial gut microflora. This determination can be made prior to administration of a regime or composition discussed herein.

Any two or more of the various embodiments described above or herein can be combined together to produce additional embodiments encompassed within the scope of the present invention.

DETAILED DESCRIPTION OF THE INVENTION

I. Definitions

Figure 1:
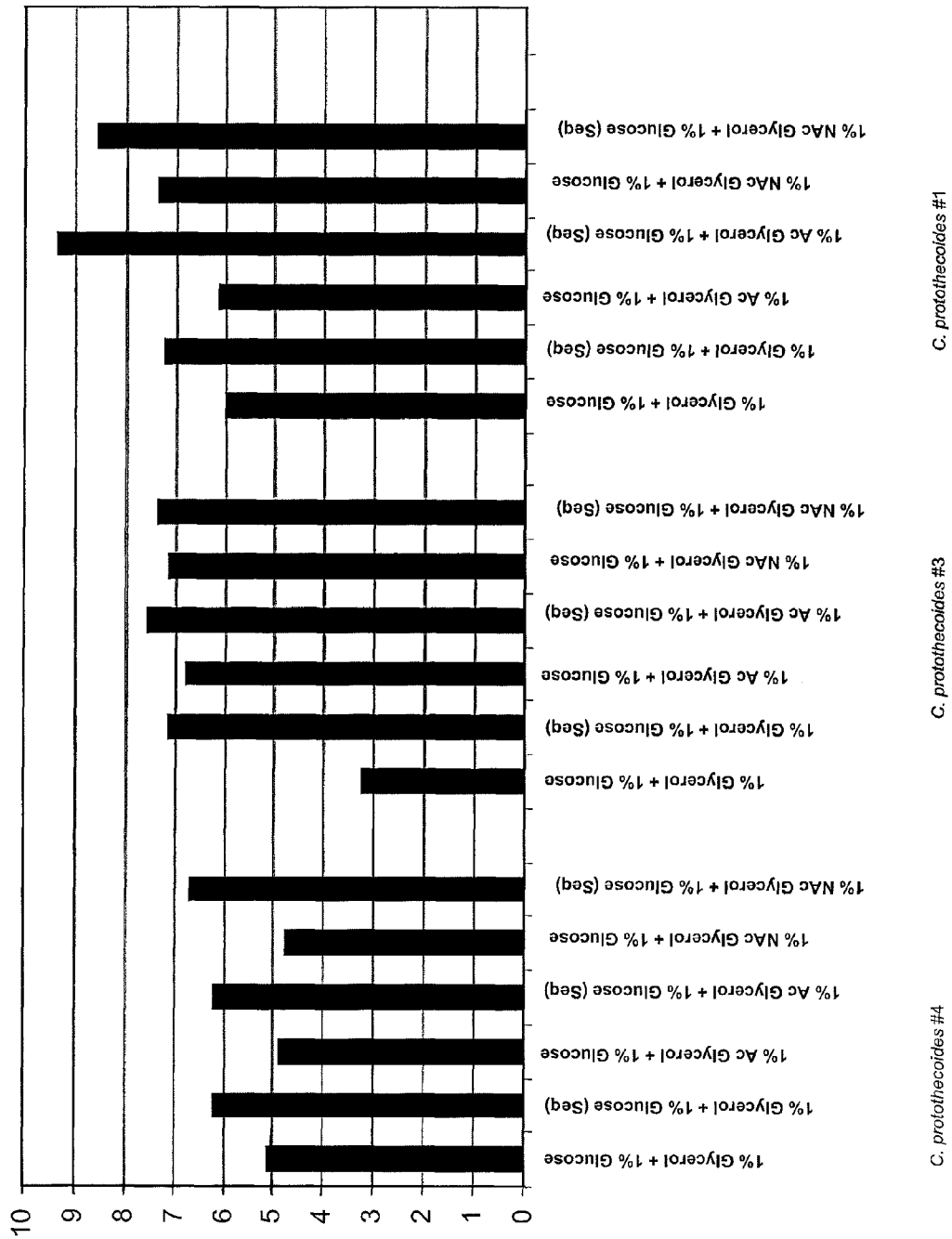
FIG. 1 shows dry cell weight per liter of multiple strains of *Chlorella protothecoides* when cultured in the presence of various types of glycerol with additional glucose, wherein glycerol is added sequentially or in combination with glucose.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "administering" refers to oral administration, unless otherwise indicated.

"Axenic" means a culture of an organism that is free from contamination by other living organisms.

"Bioreactor" means an enclosure or partial enclosure in which cells are cultured, optionally in suspension.

"Cellulosic material" means the products of digestion of cellulose, including glucose and xylose, and optionally additional compounds such as disaccharides, oligosaccharides, lignin, furfurals and other compounds. Nonlimiting examples of sources of cellulosic material include sugar caner bagasses, sugar beet pulp, corn stover, wood chips, sawdust and switchgrass.

The term "cofactor" is used herein to refer to any molecule, other than the substrate, that is required for an enzyme to carry out its enzymatic activity.

As used herein, "conventional food product" refers to a composition intended for consumption, e.g., by a human, that includes typical ingredients that one would ordinary associate with the food product. For example, a conventional cake might ordinarily include grain flour, eggs, sugar, butter, milk, and a flavoring extract. Some conventional cakes might also include fruits, nuts and/or chocolate.

As used herein, "cooked product" refers to a composition that has been heated, e.g., in an oven, for a period of time.

The term "cultivated", and variants thereof, refer to the intentional fostering of growth (increases in cell size, cellular contents, and/or cellular activity) and/or propagation (increases in cell numbers via mitosis or another method of cell division) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor. The term does not refer to the growth or propagation of microorganisms in nature or otherwise without direct human intervention.

"Diabetes," as used herein, refers to diabetes mellitus and includes type 1, type 2, and type 3 (also referred to as type 1.5) unless otherwise indicated. "Diabetes" corresponds to a fasting plasma glucose concentration greater than or equal to 126 mg/dl (6.9 mmol/l), or a plasma glucose concentration greater than or equal to 200 mg/dl (11.1 mmol/l) two hours after ingestion of a 75 g oral glucose load.

As used herein, the terms "dry weight" or "dry cell weight" refer to weight as determined in the relative absence of water. For example, reference to a component of microalgal biomass as comprising a specified percentage by dry weight means that the percentage is calculated based on the weight of the biomass after substantially all water has been removed.

As used herein, "edible ingredient" refers to any substance or composition which is fit to be eaten. "Edible ingredients" include, without limitation, grains, fruits, vegetables, proteins, herbs, spices, carbohydrates, and fats.

"Exogenously provided" describes a molecule provided to the culture media of a cell culture.

As used herein, "finished food product," or "finished food ingredient" refers to a food composition that is ready for packaging, use, or consumption. For example, a "finished food product" may have been cooked or the ingredients comprising the "finished food product" may have been mixed or otherwise integrated with one another. A "finished food product" is suitable for consumption. A "finished food ingredient" is suitable for consumption or for combination with other ingredients to form a food product.

As used herein, "food composition" refers to any composition intended to be or reasonably expected to be ingested by humans as a source of nutrition and/or calories. Food compositions are composed primarily of carbohydrates, fats, water and/or proteins and make up substantially all of a person's daily caloric intake. A "food composition" has a weight minimum that is at least ten (10) times the weight of a typical tablet or capsule (typical tablet weight ranges from 100 mg up to 1500 mg). A "food composition" is not encapsulated or in tablet form.

"Fixed carbon source" means molecule(s) containing carbon, preferably organic, that are present at ambient temperature and pressure in solid or liquid form.

"Glycerolipid profile" refers to the distribution of different carbon chain lengths and saturation levels of glycerolipids in a particular sample of biomass or oil. For example, a sample could contain glycerolipids in which approximately 60% of the glycerolipid is C18:1, 20% is C18:0, 15% is C16:0, and 5% is C14:0. In cases in which a carbon length is referenced generically, such as "C:18", such reference can include any amount of saturation; for example, microalgal biomass that contains 20% lipid as C:18 can include C18:0, C18:1, C18:2, and the like, in equal or varying amounts, the sum of which constitute 20% of the biomass.

As used herein, "good manufacturing practice" or "GMP" conditions refer to conditions established by regulations set forth at 21 C.F.R. 110 (for human food), 111 (for dietary supplements), and 210-211 (for drug products) or comparable regulatory schemes established in locales outside the United States. The U.S. regulations are promulgated by the U.S. Food and Drug Administration under the authority of the Federal Food, Drug, and Cosmetic Act to regulate manufacturers, processors, and packagers of drugs, food products and dietary supplements for human administration or consumption.

"Homogenate" means biomass that has been physically disrupted.

"Impaired fasting glucose" means a fasting plasma glucose concentration greater than or equal to 100 mg/dl (5.6 mmol/l).

"Impaired glucose tolerance" means a plasma glucose concentration greater than or equal to 140 mg/dl (7.8 mmol/l) two hours after ingestion of a 75 g oral glucose load.

As used herein, the phrase "increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

"Lipids" are a class of hydrocarbon that are soluble in nonpolar solvents (such as ether and chloroform) and are relatively or completely insoluble in water. Lipid molecules have these properties because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). "Fats" and "oils" are also known as triacylglycerides, triglycerides, triacylglycerols, or glycerolipids.

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity. The term "lysing" refers to disrupting the cellular membrane and optionally the cell wall of a biological organism or cell sufficient to release at least some intracellular content.

The term "mammal" includes, without limitation, humans, domestic animals (e.g., dogs or cats), farm animals (e.g., cows, horses, or pigs), monkeys, rabbits, mice, and laboratory animals.

As used herein, "microalgal biomass," "algal biomass," or "biomass" refers to *Chlorella protothecoides* material produced by growth and/or propagation of *Chlorella protothecoides* cells. Biomass may contain cells and/or intracellular contents as well as extracellular material. Extracellular material includes, but is not limited to, compounds secreted by a cell.

As used herein, "microalgal oil" or "algal oil" or "oil" refers to lipid components produced by *Chlorella protothecoides* cells, including triacylglycerols.

The terms "microorganism" and "microbe" are used interchangeably herein to refer to microscopic unicellular organisms.

"Patient" refers to human and non-human animals, especially mammals. Examples of patients include, but are not limited to, humans, cows, dogs, cats, goats, sheep, pigs and rabbits.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount", "therapeutically effective dose", or "effective regime" refer to the amount of *Chlorella protothecoides* biomass and schedule of administration that will elicit the desired biological or medical response of the patient or subject to which the biomass is administered. The effective amount will vary depending on the disorder or condition and its severity, as well as the age, weight, etc., of the patient or subject to be treated.

"Photobioreactor" refers to a container, at least part of which is at least partially transparent or partially open, thereby allowing light to pass through, in which one or more microalgae cells are cultured. Photobioreactors may be closed, as in the instance of a polyethylene bag or Erlenmeyer flask, or may be open to the environment, as in the instance of an outdoor pond.

As used herein, a "polysaccharide-degrading enzyme" refers to any enzyme capable of catalyzing the hydrolysis, or depolymerization, of any polysaccharide. For example, cellulases catalyze the hydrolysis of cellulose.

"Polysaccharides" (also called "glycans") are carbohydrates made up of monosaccharides joined together by glycosidic linkages. Cellulose is an example of a polysaccharide that makes up certain plant cell walls. Cellulose can be depolymerized by enzymes to yield monosaccharides such as xylose and glucose, as well as larger disaccharides and oligosaccharides.

"Port", in the context of a bioreactor, refers to an opening in the bioreactor that allows influx or efflux of materials such as gases, liquids, and cells. Ports are usually connected to tubing leading from the photobioreactor.

As used herein, "predominantly encapsulated" means that more than 50% and typically more than 75% or 90% of a referenced component, e.g., algal oil, is sequestered in a referenced container, e.g., a microalgal cell.

As used herein, "predominantly intact cells" refers to a population of cells which comprise more than 50, 75 or 90% intact cells. "Intact" refers to the physical continuity of the cellular membrane enclosing the intracellular components of the cell and means that the cellular membrane has not been disrupted in any manner that would release the intracellular components of the cell to an extent that exceeds the permeability of the cellular membrane under conventional culture conditions or those culture conditions described herein.

As used herein, "predominantly lysed" refers to a population of cells, of which more than 50%, and often more than 75 or 90% have been disrupted such that the intracellular components of the cell are no longer enclosed within the cell membrane.

The terms "prevent", "preventing", "prevention" and grammatical variations thereof as used herein, refer to a method of partially or completely delaying or precluding the onset or recurrence of a disorder or condition and/or one or more of its attendant symptoms or barring a subject from acquiring or reacquiring a disorder or condition or reducing a subject's risk of acquiring or reacquiring a disorder or condition or one or more of its attendant symptoms.

As used herein, "proximate to a meal" means within a period from approximately one hour before beginning a meal, during a meal, or up to approximately one hour after finishing a meal.

As used herein, "stover" refers to the dried stalks and leaves of a crop remaining after a grain has been harvested.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

As used herein, "uncooked product" refers to a composition that has not been subjected to heating. An "uncooked product" includes a composition that contains one or more components that were formerly subjected to heating.

Reference to proportions by volume, i.e., "v/v," means the ratio of the volume of one substance or composition to the volume of a second substance or composition. For example, reference to a composition that comprises 5% v/v microalgal oil and at least one other edible ingredient means that 5% of the composition's volume is composed of microalgal oil; e.g., a composition having a volume of 100 $mm^3$ would contain 5 $mm^3$ of microalgal oil and 95 $mm^3$ of other constituents.

Reference to proportions by weight, i.e., "w/w," means the ratio of the weight of one substance or composition to the weight of a second substance or composition. For example, reference to a composition that comprises 5% w/w microalgal biomass and at least one other edible ingredient means that 5% of the composition's weight is composed of microalgal biomass; e.g., a 100 mg composition would contain 5 mg of microalgal biomass and 95 mg of other constituents.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information.

II. General

The invention provides methods of treating a patient having impaired glucose tolerance via administration of an effective regimen of *Chlorella protothecoides* biomass comprising at least 15% algal oil by dry weight. The invention also provides methods of reducing blood glucose and/or body fat in a subject via administration of an effective regimen of *Chlorella protothecoides* biomass, as well as methods of increasing the relative abundance of beneficial gut microflora (e.g., Lactobacillales). Some aspects of the invention are premised in part on the insight that *Chlorella protothecoides* biomass can be prepared with a high oil content, and that the resulting biomass, incorporated into a food product or other dosage form, can be used to lower blood glucose levels in a subject independent of the subject's plasma insulin concentrations. Thus, in some aspects, the methods of the invention can be used to treat patient's with type 1, type 2, or type 1.5 diabetes.

The administration of *Chlorella protothecoides* biomass in accordance with the methods of the invention can be effected, in some cases, by substituting the biomass or a biomass-containing dosage form (e.g., tablets or a food product) for from 1-20% of the food by weight or calories in a patient's diet.

III. *Chlorella protothecoides*

Considerations affecting the selection of microalgae for use in the invention include, in addition to production of suitable biomass: (1) high lipid content as a percentage of cell weight; (2) ease of growth; and (3) ease of biomass processing. In some embodiments, strains of microalgae having cell walls susceptible to digestion in the gastrointestinal tract of an animal, e.g., a human, are preferred. This criterion is particularly preferred when the algal biomass is administered in an uncooked form in accordance with the present invention. Digestibility is generally decreased for microalgal strains which have a high content of cellulose/hemicellulose in the cell walls. Digestibility can be evaluated using a standard pepsin digestibility assay.

In particular embodiments, the wild-type or genetically engineered microalgae comprise cells that are at least 15%, at least 20%, at least 25%, at least 30%, at least 35%, at least 40%, at least 45%, at least 50%, at least 55%, at least 60%, at least 65%, at least 70%, at least 75%, or at least 80% or more oil by dry weight. Preferred organisms grow heterotrophically (on sugars in the absence of light) or can be engineered to do so using, for example, methods disclosed herein. The ease of transformation and availability of selectable markers and promoters, constitutive and/or inducible, that are functional in the microalgae affect the ease of genetic engineering. Processing considerations can include, for example, the availability of effective means for lysing the cells.

*Chlorella protothecoides*, when cultured heterotrophically, can contain higher oil content and impart the glucose modulation and prebiotic effects disclosed herein. *Chlorella protothecoides* is a single-celled green algae, belonging to the phylum Chlorophyta. It is spherical in shape, about 2 to 10 µm in diameter, and is without flagella.

*Chlorella protothecoides* for use in the invention can be identified by amplification of certain target regions of the genome. For example, identification of *Chlorella protothecoides* can be achieved through amplification and sequencing of nuclear and/or chloroplast DNA using primers and methodology using any region of the genome, for example using the methods described in Wu et al., *Bot. Bull. Acad. Sin.* 42:115-121 (2001). Well established methods of phylogenetic analysis, such as amplification and sequencing of ribosomal internal transcribed spacer (ITS1 and ITS2 rDNA), 18S rRNA, 23S rRNA, and other conserved genomic regions can be used by those skilled in the art to identify species and strain. For general examples of methods of identification and classification of algae see *Genetics*, 170(4):1601-10 (2005) and RNA, 11(4):361-4 (2005).

Genomic DNA comparison can also be useful to identify *Chlorella protothecoides* strains that have been misidentified in a strain collection. Often a strain collection will identify species of microalgae based on phenotypic and morphological characteristics. The use of these characteristics may lead to miscategorization of the species or genus of a microalgae. The use of genomic DNA comparison can be a better method of identifying *Chlorella protothecoides* strains that are suitable for use in the present invention. Specific examples using genotyping data to establish phylogenetic relationship/identity for eight *Chlorella protothecoides* strains from different collections are described below in the Examples.

In some cases, microalgae that are preferred for use in the present invention have genomic DNA sequences encoding for 23S rRNA that have no more than 1 base pair, no more than 2 base pairs, no more than 3 base pairs, no more than 4 base pairs, no more than 5 base pairs, no more than 6 base pairs, no more than 7 base pairs, no more than 8 base pairs, no more than 9 base pairs or no more than 10 base pairs difference to that of the sequences listed in SEQ ID NO: 5 or SEQ ID NO:6.

IV. Methods of Culturing *Chlorella protothecoides*

*Chlorella protothecoides* can be cultured for production of algal biomass. Culture for purposes of biomass production is usually conducted on a large scale. Preferably a fixed carbon source is present. The culture can also be exposed to light some or all of the time.

*Chlorella protothecoides* can be cultured in liquid media. The culture can be contained within a bioreactor. Optionally, the bioreactor does not allow light to enter. Alternatively, cells can also be cultured in photobioreactors that contain a fixed carbon source and allow light to strike the cells. Culture condition parameters can be manipulated to optimize total oil production, the combination of lipid species produced, and/or production of a specific oil. In some instances it is preferable to culture cells in the dark, such as, for example, when using extremely large (40,000 liter and higher) fermentors that do not allow light to strike the culture.

Culture media typically contains components such as a fixed nitrogen source, trace elements, optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6MO_7O_{24}.4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, glucuronic acid, and/or acetate. The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Some microalgae species can grow by utilizing a fixed carbon source such as glucose or acetate in the absence of light. Such growth is known as heterotrophic growth. For *Chlorella protothecoides*, for example, heterotrophic growth results in high production of biomass and accumulation of high lipid content in cells.

Other culture parameters can also be manipulated, such as the pH of the culture media, the identity and concentration of trace elements, and other media constituents.

A. Photosynthetic Growth

Microalgae can be grown in the presence of light. The number of photons striking a culture of microalgae cells can be manipulated, as well as other parameters such as the wavelength spectrum and ratio of dark:light hours per day. Microalgae can also be cultured in natural light, as well as simultaneous and/or alternating combinations of natural light and artificial light. For example, microalgae of the genus *Chlorella* can be cultured under natural light during daylight hours and under artificial light during night hours.

The gas content of a photobioreactor to grow microorganisms like microalgae can be manipulated. Part of the volume of a photobioreactor can contain gas rather than liquid. Gas inlets can be used to pump gases into the photobioreactor. Any gas can be pumped into a photobioreactor, including air, air/$CO_2$ mixtures, noble gases such as argon and others. The rate of entry of gas into a photobioreactor can also be manipulated. Increasing gas flow into a photobioreactor increases the turbidity of a culture of microalgae. Placement of ports conveying gases into a photobioreactor can also affect the turbidity of a culture at a given gas flow rate. Air/$CO_2$ mixtures can be modulated to generate optimal amounts of $CO_2$ for maximal growth by a particular organism. Microalgae grow significantly faster in the light under, for example, 3% $CO_2$/97% air than in 100% air. 3% $CO_2$/97% air is approximately 100-fold more $CO_2$ than found in air. For example, air:$CO_2$ mixtures of about 99.75% air:0.25% $CO_2$, about 99.5% air:0.5% $CO_2$, about 99.0% air:1.00% $CO_2$, about 98.0% air:2.0% $CO_2$, about 97.0% air:3.0% $CO_2$, about 96.0% air:4.0% $CO_2$, and about 95.00% air:5.0% $CO_2$ can be infused into a bioreactor or photobioreactor.

Microalgae cultures can also be subjected to mixing using devices such as spinning blades and impellers, rocking of a culture, stir bars, infusion of pressurized gas, and other instruments.

Photobioreactors can have ports allowing entry of gases, solids, semisolids and liquids into the chamber containing the microalgae. Ports are usually attached to tubing or other means of conveying substances. Gas ports, for example, convey gases into the culture. Pumping gases into a photobioreactor can serve to both feed cells $CO_2$ and other gases and to aerate the culture and therefore generate turbidity. The amount of turbidity of a culture varies as the number and position of gas ports is altered. For example, gas ports can be placed along the bottom of a cylindrical polyethylene bag. Microalgae grow faster when $CO_2$ is added to air and bubbled into a photobioreactor.

Photobioreactors can be exposed to one or more light sources to provide microalgae with light as an energy source via light directed to a surface of the photobioreactor. Preferably the light source provides an intensity that is sufficient for the cells to grow, but not so intense as to cause oxidative damage or cause a photoinhibitive response. In some instances a light source has a wavelength range that mimics or approximately mimics the range of the sun. In other instances a different wavelength range is used. Photobioreactors can be placed outdoors or in a greenhouse or other facility that allows sunlight to strike the surface, such as the use of *Chlorella protothecoides* in photobioreactors described in U.S. patent 20080160591.

Photobioreactors preferably have one or more ports that allow media entry. It is not necessary that only one substance enter or leave a port. For example, a port can be used to flow culture media into the photobioreactor and then later can be used for sampling, gas entry, gas exit, or other purposes. In some instances a photobioreactor is filled with culture media at the beginning of a culture and no more growth media is infused after the culture is inoculated. In other words, the microalgal biomass is cultured in an aqueous medium for a period of time during which the microalgae reproduce and increase in number; however quantities of aqueous culture medium are not flowed through the photobioreactor throughout the time period. Thus in some embodiments, aqueous culture medium is not flowed through the photobioreactor after inoculation.

In other instances culture media can be flowed though the photobioreactor throughout the time period during which the microalgae reproduce and increase in number. In some embodiments media is infused into the photobioreactor after inoculation but before the cells reach a desired density. In other words, a turbulent flow regime of gas entry and media entry is not maintained for reproduction of microalgae until a desired increase in number of said microalgae has been achieved.

Photobioreactors preferably have one or more ports that allow gas entry. Gas can serve to both provide nutrients such as $CO_2$ as well as to provide turbulence in the culture media. Turbulence can be achieved by placing a gas entry port below the level of the aqueous culture media so that gas entering the photobioreactor bubbles to the surface of the culture. One or more gas exit ports allow gas to escape, thereby preventing pressure buildup in the photobioreactor. Preferably a gas exit port leads to a "one-way" valve that prevents contaminating microorganisms from entering the photobioreactor. In some instances cells are cultured in a photobioreactor for a period of time during which the microalgae reproduce and increase in number, however a turbulent flow regime with turbulent eddies predominantly throughout the culture media caused by gas entry is not maintained for all of the period of time. In other instances a turbulent flow regime with turbulent eddies predominantly throughout the culture media caused by gas entry can be maintained for all of the period of time during which the microalgae reproduce and increase in number. In some instances a predetermined range of ratios between the scale of the photobioreactor and the scale of eddies is not maintained for the period of time during which the microalgae reproduce and increase in number. In other instances such a range can be maintained.

Photobioreactors preferably have at least one port that can be used for sampling the culture. Preferably a sampling port can be used repeatedly without altering compromising the axenic nature of the culture. A sampling port can be configured with a valve or other device that allows the flow of sample to be stopped and started. Alternatively a sampling port can allow continuous sampling. Photobioreactors preferably have at least one port that allows inoculation of a culture. Such a port can also be used for other purposes such as media or gas entry.

B. Heterotrophic Growth

As an alternative to photosynthetic growth of microorganisms, as described above, some microorganisms can be cultured under heterotrophic growth conditions in which a fixed carbon source provides energy for growth and lipid accumulation. In some cases, the fixed carbon energy source comprises cellulosic material, including depolymerized cellulosic material, a 5-carbon sugar, or a 6-carbon sugar.

Standard methods for the heterotrophic growth and propagation of *Chlorella protothecoides* are known (see for example Miao and Wu, *J. Biotechnology*, 2004, 11:85-93). Under certain heterotrophic conditions with nitrogen starvation, *Chlorella protothecoides* can produce up to 55% lipid (as measured by dry cell weight (DCW) (Miao and Wu, *Biosource Technology* (2006) 97:841-846). Glucose and nitrogen conditions are also important for the generation of increased biomass and lutein in *Chlorella protothecoides* (Shi et al., *Enzy Microbio Tech*, (2000) 27:312-318 and Shi et al., *Process Biochem*, (1999) 34: 341-347). The invention also provides novel growth conditions for *Chlorella*. For example, multiple strains of *Chlorella protothecoides* can be grown in the presence of glycerol. Examples below describe specific culture conditions of *Chlorella protothecoides* grown on glycerol as a carbon source. FIG. 1 shows high lipid accumulation (DCW) in *Chlorella protothecoides* when grown on a combination of glucose and glycerol. The percent of dry cell weight as lipid can be modulated by the length of time the cells are cultured in a given culture media that is replete with a fixed carbon source under conditions of limited nitrogen. In general, the longer the cells are held in such conditions the higher the percent lipid as dry cell weight becomes.

The invention provides significantly improved culture parameters incorporating the use of glycerol for fermentation of multiple genera of microalgae. As the Examples demonstrate, many *Chlorella protothecoides* strains grow very well on not only purified reagent-grade glycerol, but also on acidulated and non-acidulated glycerol byproduct from biodiesel transesterification. In some instances, microalgae, such as *Chlorella* strains, undergo cell division faster in the presence of glycerol than in the presence of glucose. In these instances, two-stage growth processes in which cells are first fed glycerol to rapidly increase cell density, and are then fed glucose to accumulate lipids can improve the efficiency with which lipids are produced.

Other feedstocks for culturing microalgae in accordance with the present invention are provided as well, such as mixtures of glycerol and glucose, mixtures of glucose and xylose, mixtures of fructose and glucose, sucrose, glucose, fructose, xylose, arabinose, mannose, galactose, acetate, and molasses. Also provided are methods utilizing corn stover, sugar beet pulp, and switchgrass in combination with depolymerization enzymes. The use of these alternative feedstocks is demonstrated in the Examples provided herein.

For lipid and oil production, cells, including recombinant cells of the invention described herein, are preferably cultured or fermented in large quantities. The culturing may be in large liquid volumes, such as in suspension cultures as an example. Other examples include starting with a small culture of cells which expand into a large biomass in combination with cell growth and propagation as well as lipid and oil production. Bioreactors or steel fermentors can be used to accommodate large culture volumes. A fermentor similar those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, molasses, or the like; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other starch (glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of lipid-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

Oil production by cells disclosed herein can occur during the log phase or thereafter, including the stationary phase wherein nutrients are supplied, or still available, to allow the continuation of oil and lipid production in the absence of cell division.

Preferably, microorganisms grown using conditions described herein and known in the art comprise at least about 15% by dry weight of lipid, preferably at least about 25% to about 35% by dry weight, more preferably at least about 45% by dry weight, and most preferably at least about 55% by dry weight.

FIG. 1 demonstrates three different strains of *Chlorella protothecoides* accumulating higher dry cell weight per liter of culture when glycerol and glucose are added sequentially than when the same quantities of glycerol and glucose are added together at the beginning of the experiment. This trend was observed when acidulated biodiesel byproduct glycerol, non-acidulated biodiesel byproduct glycerol, or reagent grade glycerol was used.

Three different markers of productivity (dry cell weight per liter, grams per liter of lipid, and percentage of dry cell weight as lipid) in microbial lipid production are improved by the use of biodiesel byproduct and temporal separation of carbon sources. The invention therefore provides novel methods of generating higher quantities of lipid per unit time in multiple species of microbes from highly divergent areas of the evolutionary tree, including both prokaryotes and eukaryotes. The methods of manufacturing lipids and oils disclosed herein using glycerol are not limited to microalgae, but can be used with any microbe capable of utilizing glycerol as an energy source.

In an alternate heterotrophic growth method in accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstock have been found to be inhibitory to yeast growth, and yeast cannot use the 5-carbon sugars produced from cellulosic materials (e.g., xylose from hemi-cellulose). By contrast, microalgae can grow on processed cellulosic material. Accordingly, the invention provides a method of culturing a microalgae in the presence of a cellulosic material and/or a 5-carbon sugar. Cellulosic materials generally include:

| Component | Percent Dry Weight |
|---|---|
| Cellulose | 40-60% |
| Hemicellulose | 20-40% |
| Lignin | 10-30% |

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

Figure 2:
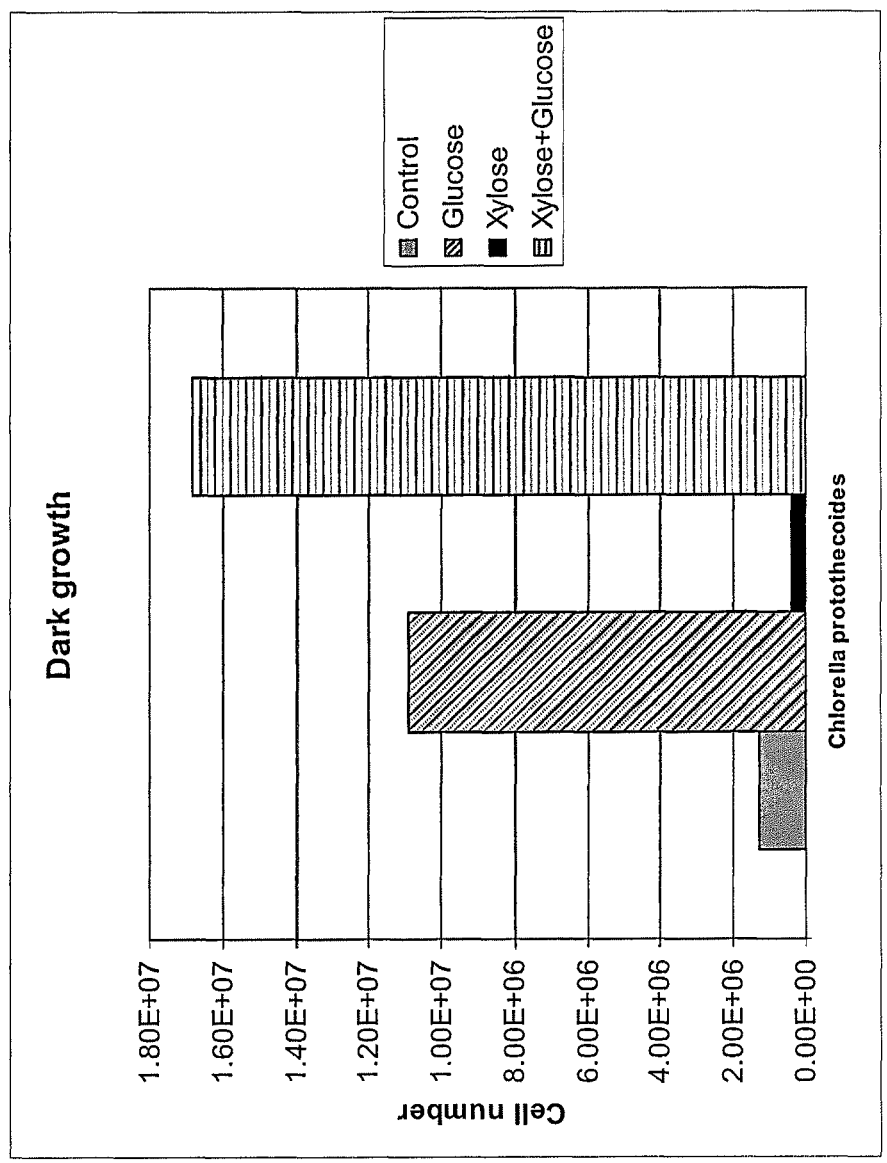
FIG. 2 shows a synergistic effect of a combination of xylose and glucose on growth of *Chlorella* compared to xylose or glucose alone.

Surprisingly, *Chlorella protothecoides* have been shown herein to exhibit higher levels of productivity when cultured on a combination of glucose and xylose than when cultured on either glucose or xylose alone. This synergistic effect provides a significant advantage in that it allows cultivation of *Chlorella protothecoides* on combinations of xylose and glucose, such as cellulosic material, and is shown in FIG. 2.

In still another alternative heterotrophic growth method in accordance with the present invention, which itself may optionally be used in combination with the methods described above, sucrose, produced by example from sugar cane or sugar beet, is used as a feedstock.

In still another alternative heterotrophic growth method in accordance with the present invention, which itself may optionally be used in combination with the methods described above, sucrose, produced by example from sugar cane or sugar beet, is used as a feedstock. Some microalgae may need an exogenous sucrose utilization enzyme, such as a sucrose invertase, to be added to the culture medium in order to utilize the sucrose as a carbon source.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and lipid production. In addition, the invention includes the selection and/or genetic engineering of microbes, such as microalgae, to produce microbes that are even more suitable for use in the above-described methods. For example, the microbes having a greater ability to utilize any of the above-described feedstocks for increased proliferation and/or lipid production are within the scope of the invention.

C. Mixotrophic Growth

Mixotrophic growth is the use of both light and fixed carbon source(s) as energy sources for cells to grow and produce oils. Mixotrophic growth can be conducted in a photobioreactor. Microalgae can be grown and maintained in closed photobioreactors made of different types of transparent or semitransparent material. Such material can include Plexiglas® enclosures, glass enclosures, bags made from substances such as polyethylene, transparent or semitransparent pipes, and other materials. Microalgae can be grown and maintained in open photobioreactors such as raceway ponds, settling ponds, and other non-enclosed containers.

D. Growth Media

Microorganisms useful in accordance with the methods of the present invention are found in various locations and environments throughout the world. As a consequence of their isolation from other species and their resulting evolutionary divergence, the particular growth medium for optimal growth and generation of oil and/or lipid can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin for its culture collection of algae (UTEX). For example, various fresh water and salt water media include those shown in Table 1, below.

TABLE 1

Exemplary Algal Media.

| Fresh Water Media | Salt Water Media |
|---|---|
| ½ CHEV Diatom Medium | 1% F/2 |
| ⅓ CHEV Diatom Medium | ½ Enriched Seawater Medium |
| ⅕ CHEV Diatom Medium | ½ Erdschreiber Medium |
| 1:1 DYIII/PEA + Gr+ | ½ Soil + Seawater Medium |
| ⅔ CHEV Diatom Medium | ⅓ Soil + Seawater Medium |
| 2X CHEV Diatom Medium | ¼ ERD |
| Ag Diatom Medium | ¼ Soil + Seawater Medium |
| Allen Medium | ⅕ Soil + Seawater Medium |
| BG11-1 Medium | ⅔ Enriched Seawater Medium |
| Bold 1NV Medium | 20% Allen + 80% ERD |
| Bold 3N Medium | 2X Erdschreiber's Medium |
| *Botryococcus* Medium | 2X Soil + Seawater Medium |
| Bristol Medium | 5% F/2 Medium |
| CHEV Diatom Medium | ⅗ Soil + Seawater Agar Medium |
| Chu's Medium | Artificial Seawater Medium |
| CR1 Diatom Medium | BG11-1 + .36% NaCl Medium |
| CR1+ Diatom Medium | BG11-1 + 1% NaCl Medium |
| CR1-S Diatom Medium | Bold 1NV:Erdshreiber (1:1) |
| *Cyanidium* Medium | Bold 1NV:Erdshreiber (4:1) |
| *Cyanophycean* Medium | Bristol-NaCl Medium |
| Desmid Medium | Dasycladales Seawater Medium |
| DYIII Medium | Enriched Seawater Medium |
| *Euglena* Medium | Erdschreiber's Medium |
| HEPES Medium | ES/10 Enriched Seawater Medium |
| J Medium | ES/2 Enriched Seawater Medium |
| Malt Medium | ES/4 Enriched Seawater Medium |
| MES Medium | F/2 Medium |
| Modified Bold 3N Medium | F/2 + NH4 |
| Modified COMBO Medium | LDM Medium |
| N/20 Medium | Modified 2 X CHEV |
| *Ochromonas* Medium | Modified 2 X CHEV + Soil |
| P49 Medium | Modified Artificial Seawater Medium |
| *Polytomella* Medium | Modified CHEV |
| Proteose Medium | Porphridium Medium |
| Snow Algae Media | Soil + Seawater Medium |
| Soil Extract Medium | SS Diatom Medium |
| Soilwater: BAR Medium | |
| Soilwater: GR– Medium | |
| Soilwater: GR–/NH4 Medium | |
| Soilwater: GR+ Medium | |
| Soilwater: GR+/NH4 Medium | |
| Soilwater: PEA Medium | |
| Soilwater: Peat Medium | |
| Soilwater: VT Medium | |
| *Spirulina* Medium | |
| Tap Medium | |
| *Trebouxia* Medium | |
| Volvocacean Medium | |
| Volvocacean-3N Medium | |
| *Volvox* Medium | |
| *Volvox*-Dextrose Medium | |
| Waris Medium | |
| Waris + Soil Extract Medium | |

In a particular example, a medium suitable for culturing *Chlorella protothecoides* (UTEX 31) comprises Proteose Medium. This medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use.

Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic).

E. Increasing Yield of Lipids

Process conditions can be adjusted to increase the yield of lipids suitable for a particular use and/or to reduce production cost. For example, in certain embodiments, a microbe (e.g., a microalgae) is cultured in the presence of a limiting concentration of one or more nutrients, such as, for example, carbon and/or nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 20%, 30%, 40%, 50%, 75%, 100%, 200%, 300%, 400%, or 500%. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period.

To increase lipid yield, acetic acid can be employed in the feedstock for a lipid-producing microbe (e.g., a microalgae). Acetic acid feeds directly into the point of metabolism that initiates fatty acid synthesis (i.e., acetyl-CoA); thus providing acetic acid in the culture can increase fatty acid production. Generally, the microbe is cultured in the presence of a sufficient amount of acetic acid to increase microbial lipid yield, and/or microbial fatty acid yield, specifically, over microbial lipid (e.g., fatty acid) yield in the absence of acetic acid.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin or pantothenate. Genes encoding cofactors suitable for use in the invention or that participate in the synthesis of such cofactors are well known and can be introduced into microbes (e.g., microalgae), using constructs and techniques such as those described herein.

V. Methods of Preparing Microalgal Biomass from Algal Cultures

*Chlorella protothecoides* cultures generated according to the methods described herein yield microalgal biomass suitable for use in the methods and compositions of the present invention. At the point of harvesting the microalgal biomass from the culture, the biomass comprises predominately intact cells suspended in an aqueous culture medium. The culture medium can be drained off or the biomass otherwise removed from the culture medium and subjected to further optional processing, as described below. Optionally, separation of the biomass from the culture medium can be effected by centrifugation to generate a concentrated paste comprising the cells. Centrifugation does not remove significant amounts of intracellular water. Microalgal biomass can be processed to produce a powder, flakes, or a vacuum-packed cake, in exemplary embodiments.

The processes described below can be performed according to GMP conditions in accordance with applicable U.S. or foreign regulations.

A. Drying Biomass

In some cases, drying the microalgal biomass is advantageous to facilitate further processing or for use of the biomass in the methods and compositions described herein. Drying the biomass generated from the cultured microalgae described herein removes water that may be an undesirable component of the dosage forms described herein. Drying the biomass is an optional process step.

In some cases, the biomass can be dried using a drum dryer in which the biomass is rotated in a drum and dried with the application of air, which may be heated to expedite the drying process. In other cases, an oven or spray drying can be used to facilitate drying of the biomass. Alternatively, the biomass may be dried via a lyophilization process. The lyophilization process can summarily be described as a "freeze-drying" process, in which the biomass is frozen in a freeze-drying chamber to which a vacuum is applied. The application of a vacuum to the freeze-drying chamber results in sublimation (primary drying) and desorption (secondary drying) of the water from the biomass, resulting in a product for further processing in accordance with the methods described herein.

B. Lysing Cells

In those instances in which biomass comprising other than predominantly intact cells is desired for use in the methods or compositions of the present invention, an optional process step of lysing the cells can be performed. When the cells have been cultured for a desired period or to a desired density, and separated from the culture medium, the cells may be lysed to provide a homogenated biomass or to facilitate extraction of microalgal oil.

In some cases, the biomass is washed with a washing solution (e.g., DI water) to get rid of the fermentation broth and debris prior to cell disruption. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microalgae containing lipids can be lysed to produce a lysate. The step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially.

The extent of cell disruption can be observed by microscopic analysis. Using one or more of the methods described herein, typically more than 70% cell breakage is observed. Preferably, cell breakage is more than 80%, more preferably more than 90% and most preferred about 100%.

C. GMP Conditions

The processes described herein can be performed in accordance with GMP regulations. In the United States, GMP regulations for manufacturing, processing, packaging and holding drug products for administration to humans or animals are codified at 21 CFR 210-211. In some embodiments in accordance with the invention, microalgal biomass can be administered in the form of a food product. As applicable, GMP regulations for manufacturing, packing, or holding human food are codified at 21 CFR 110. The provisions related to drugs and food products, including all parts thereof, as well as ancillary provisions referenced therein, are hereby incorporated by reference in their entirety for all purposes.

In the context of drug products, GMP conditions in the United States or in other jurisdictions include adherence to regulations setting forth quality control requirements for manufacturing, processing, packaging and holding drug products, as well as providing qualification and responsibility requirements for personnel engaged in these activities, and for the design and maintenance of facilities and equipment used in the performance of these activities, among other things.

In the context of food products, GMP conditions apply in determining whether a food is adulterated in that the food has been manufactured under such conditions that it is unfit for food, or in that the food has been prepared, packed, or held under insanitary conditions whereby it may have become contaminated with filth, or whereby it may have been rendered injurious to health. GMP conditions can include adherence to regulations governing: disease control, cleanliness and training of personnel; maintenance and sanitary operation of facilities and equipment; provision of appropriate quality control procedures to prevent contamination from any source; and storage and transportation of finished food under conditions that will protect food against physical, chemical, or undesirable microbial contamination, as well as against deterioration of the food and the container.

VI. Composition of Microalgal Biomass and Algal Oil

The microalgal biomass generated by the culture methods described herein comprises microalgal oil as well as other constituents generated by the microorganisms or incorporated by the microorganisms from the culture medium during fermentation.

A. Oil Content

*Chlorella protothecoides* microalgal biomass generated by the culture methods described herein and useful in accordance with the present invention comprises at least 15% microalgal oil by dry weight. In some embodiments, the microalgal biomass comprises at least 25%, at least 35%, at least 45%, at least 50%, at least 55%, or at least 60% microalgal oil by dry weight. In some embodiments, the microalgal biomass contains from 15-90% microalgal oil, from 25-75% microalgal oil, from 40-75% microalgal oil, or from 50-70% microalgal oil by dry weight.

In various embodiments, the microalgal biomass comprises at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50% microalgal oil by dry weight. In other embodiments, the microalgal biomass comprises at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, or at least 90% microalgal oil by dry weight.

B. Oil Composition

The oil of the *Chlorella protothecoides* biomass described herein for use in the methods and compositions of the present invention can comprise glycerolipids with one or more distinct fatty acid ester side chains. Glycerolipids are comprised of a glycerol molecule esterified to one, two, or three fatty acid molecules, which can be of varying lengths and have varying degrees of saturation.

In some embodiments, the microalgal oil is primarily comprised of monounsaturated oil. In some cases, the algal oil is at least 50% monounsaturated oil by weight. In various embodiments, the algal oil is at least 50%, at least 55%, at least 60%, at least 65%, at least 70%, at least 75%, or at least 80% or more monounsaturated oil by weight or by volume. In some embodiments, the microalgal oil comprises at least 10%, at least 20%, at least 30%, at least 40%, or at least 50% or more esterified oleic acid or esterified alpha-linolenic acid by weight of by volume. The algal oil comprises less than 1% by weight or by volume, or is substantially free of, esterified docosahexanoic acid (DHA).

In some cases, the microalgal biomass comprises algal oil predominantly encapsulated in cells of the biomass. In other cases, the biomass comprises predominantly lysed cells and the algal oil is thus primarily not encapsulated in microalgal cells.

C. Other Constituents

*Chlorella protothecoides* microalgal biomass can also include other constituents produced by the microalgae, or incorporated into the microalgae from the culture medium. These other constituents can be present in varying amounts.

The other constituents can include, without limitation, phospholipids (e.g., algal lecithin), carbohydrates, glycoproteins, phytosterols (e.g., β-sitosterol, campesterol, stigmasterol, ergosterol, and brassicasterol), tocopherols, tocotrienols, carotenoids (e.g., α-carotene, β-carotene, and lycopene), xanthophylls (e.g., lutein, zeaxanthin, α-cryptoxanthin, and β-cryptoxanthin), proteins, polysaccharides, and various organic or inorganic compounds (e.g., selenium).

VII. Methods of Treating Impaired Glucose Metabolism

In one aspect, the present invention is directed to a method of treating a patient having impaired glucose metabolism. In other embodiments, the patient has a condition such as impaired glucose tolerance, dysglycemia, insulin resistance, cardiovascular disease, diabetes, hyperglycemia, insulin deficiency, and/or metabolic syndrome. In these and other embodiments, the methods involve first diagnosing that the patient is in need of treatment (i.e., exhibits a symptom of one or more of the following conditions), and then, administering an effective regime of *Chlorella prototheocoides* biomass such that the symptom(s) lessen or go away completely. In one embodiment, the method comprises administering to the patient an effective regime of *Chlorella prototheocoides* biomass comprising at least 15% algal oil by dry weight. In some cases, methods of the invention comprise reducing blood glucose levels in a subject relative to a level prior to treatment with the algal biomass regime. In other cases, methods of the invention comprise reducing the percentage fat of total body weight of the subject relative to the percentage fat of total body weight before administering the algal biomass regime.

In some cases, a patient's impaired glucose metabolism is identified as impaired glucose tolerance. As defined herein, impaired glucose tolerance corresponds to a glucose concentration of 140 mg/dl (7.8 mmol/l) or more, as measured by an oral glucose tolerance test (OGTT). An OGTT is a routine assay used to assess an individual's capacity to metabolize a bolus of glucose. Typically, the patient ingests a 75 g glucose load, and an assessment of plasma glucose concentration is made 2 hours after ingestion.

In other cases, a patient's impaired glucose metabolism is identified as impaired fasting glucose. As defined herein, impaired fasting glucose corresponds to a glucose concentration of 100 mg/dl (5.6 mmol/l) or more, as measured by a fasting plasma glucose test (FPGT). An FPGT is a routine assay used to assess an individual's plasma glucose concentration following a fasting period of at least 8 hours.

In still other cases, a patient's impaired glucose metabolism is identified as diabetes mellitus. A diagnosis of diabetes may be made with reference to a FPGT or an OGTT, or via other criteria as determined by a patient's physician. Diabetes mellitus includes types 1, 2, and 3 (also referred to as type 1.5). With reference to the assays identified above, diabetes corresponds to a plasma glucose concentration greater than or equal to 126 mg/dl (6.9 mmol/l) in the FPGT, or a plasma glucose concentration greater than or equal to 200 mg/dl (11.1 mmol/l) in the OGTT.

In those instances in which a patient's glucose concentration exceeds the normal level (i.e., 99 mg/dl for a FPGT, or 125 mg/dl for an OGTT), but is not high enough to be classified as diabetes, the patient may be referred to as having a condition known as pre-diabetes. Left untreated, in many instances individuals with pre-diabetes will develop non-insulin dependent diabetes. See Keen et al., *Diabetologia* 22:73-78 (1982).

In some cases, as demonstrated in Example 9, administration of algal biomass in accordance with the present invention results in a reduction in the mean plasma glucose concentration of a mammal relative to the concentration before administration of the algal biomass. In some cases, the mean plasma glucose concentration is lowered 10-50%. In some cases, the mean plasma glucose concentration is lowered 10-40%, 20-40%, 30-40%, or 40-50%. In some cases, the reduction in mean plasma glucose concentration is at least 5%, at least 10%, at least 15%, at least 20%, at least 25%, at least 30%, at least 35%, at least 40%, at least 45%, or at least 50%. In some cases, the mean plasma glucose concentration is lowered from above the diabetic threshold to below the diabetic threshold or below the pre-diabetic threshold. In other cases, the mean plasma glucose concentration is lowered from above the pre-diabetic threshold to below the pre-diabetic threshold. In each case, the "threshold" refers to the plasma glucose concentrations discussed above with reference to the FPGT and the OGTT.

Methods of treating impaired glucose metabolism include both therapeutic and prophylactic treatment unless otherwise specified. For example, in cases in which a patient is diagnosed with diabetes, it is desirable to treat the patient to achieve a therapeutically effective result, i.e., a reduction in the individual's plasma glucose concentration to a level below that classified as diabetic. Alternatively, in cases in which a patient is diagnosed with a glucose intolerance characterized as pre-diabetes, it is desirable to treat the patient via the methods of the present invention to prevent the individual's plasma glucose level from rising to a level classified as diabetic, as well as reducing the individual's plasma glucose level to or toward the normal range of plasma glucose concentrations. In some cases, use of the methods described herein can be combined with other lifestyle changes, such as increased exercise, to reduce plasma glucose levels from diabetic or pre-diabetic levels to within the normal range. Some methods of the present invention further comprise monitoring blood glucose levels of the patient (e.g., via a FPGT or an OGTT) to assess the patient's response to the algal biomass treatment and the need for further administration.

In some cases, an alternative treatment for diabetes (e.g., a non-algal pharmaceutical product), administered to a patient prior to treatment according to the methods of the present invention, can be reduced or eliminated after treatment with *Chlorella prototheocoides* microalgal biomass. In some cases, the alternative treatment comprises a pharmaceutical composition such as insulin, sulfonylureas (e.g., glimepiride, glipizide, or tolazamide), biguanides (e.g., metformin), thiazolidinediones (e.g., pioglitazone or rosiglitazone), alpha glucosidase inhibitors (e.g., miglitol or acarbose), D-phenylalanine derivatives (e.g., nateglinide), Dipeptidyl peptidase-4 inhibitors (e.g., sitagliptin phosphate), or amylin or incretin mimetics (e.g., pramlintide acetate or exenatide, respectively). In other cases, the alternative treatment is a non-algal dietary regime, dietary restrictions, or an exercise regime.

In some methods, a reduction in the mean plasma glucose concentration is accompanied by a reduction in the percentage fat of total body weight in the patient relative to the percentage prior to administration of the algal biomass in accordance with the present invention. In some cases, the percentage fat of total body weight is reduced by at least 1%, at least 2%, at least 3%, at least 4%, at least 5%, at least 6%, at least 7%, at least 8%, at least 9%, or at least 10% relative to the percentage fat of total body weight prior to administration of the algal biomass.

In some methods in accordance with the present invention, *Chlorella prototheocoides* microalgal biomass comprising at least 15% algal oil is administered to a subject with a body mass index (BMI) of greater than 24.9 or greater than 29.9 to reduce the percentage fat of total body weight and thereby reduce the individual's BMI relative to the BMI prior to administration of the algal biomass. The BMI is a single number that evaluates an individual's weight status in relation to height, and is highly correlated with body fat. Being overweight (characterized as a BMI of 25-29.9) or obese (characterized as a BMI of 30-39.9, or greater than 40 (extreme obesity)) is a significant factor in the development and/or prolongation of impaired glucose metabolism, including type 2 diabetes. Ioannidis, I., *Angiology* 59(2 Suppl):39S-43S (2008), and Keller, U., *Int J Vitam Nutr Res.* 76(4):172-177 (2006).

A reduction in the percentage fat of total body weight in an individual, as discussed herein, will generally result in a reduction in the individual's BMI as well. In some cases, an individual's BMI is reduced from a level indicating obesity or overweight to a level indicating a normal weight relative to height. Some methods of the present invention further comprise monitoring a patient's percentage body fat and/or BMI to assess the patient's response to the algal biomass treatment and the need for further administration.

In some embodiments, the reduced plasma glucose concentration and/or the reduction in percentage body fat is accompanied by an increase in the relative abundance of beneficial gut microflora, as discussed in greater detail below.

VIII. Methods of Increasing the Relative Abundance of Beneficial Gut Microflora In another aspect, the present invention is directed to a method of increasing the relative abundance of beneficial gut microflora in a subject. In one embodiment, the method comprises first determining that the subject could benefit from treatment to increase the abundance of beneficial gut microflora and then administering to the subject an effective regime of *Chlorella protothecoides* microalgal biomass comprising at least 15% algal oil by dry weight. In such methods, the microalgal biomass comprises a prebiotic, which supports an increase in the relative abundance of particular microorganisms in the gastrointestinal tract of the individual subject.

A prebiotic, in contrast to a probiotic, which traditionally comprise a dietary supplement containing the desired beneficial bacteria or yeast cells, is a composition that promotes the growth and propagation of particular species of microorganisms without actually ingesting the microbes themselves. Lactobacillales are an order of gram-positive bacteria that comprise lactic acid bacteria, and are widely used in the production of fermented foods, including dairy products such as yogurt and cheese.

Approximately 100 species of microorganisms and 100 trillion or more individual microorganisms live in the human intestines and form the intestinal bacteria plexus. Intestinal bacteria, such as *Lactobacillus bifidus* and the like, have a strong relationship with the health of humans, while others have a detrimental effect on the body. The distribution of these flora varies with factors such as age, race, lifestyle, environment, diet, and the like. Intestinal flora in particular are markedly affected by daily diet. Consequently, diet has been promoted as of particular importance in the control of intestinal conditions. Commercial milk products, such as yogurt, containing *Lactobacillus bifidus* for balanced intestinal function have been widely used for many years. By means of these products, viable lactic acid bacteria are ingested in order to balance intestinal function (e.g., preventing constipation).

As demonstrated in Example 10 below, administration of a diet comprising algal biomass derived from cultured *Chlorella protothecoides* results in a relative increase in the presence of gut microflora belonging to the class Lactobacillales. The algal biomass functions as a prebiotic to promote the propagation of these beneficial microorganisms.

In some embodiments, methods in accordance with the present invention further comprise monitoring the relative abundance of gut microflora in a subject to detect an increase in Lactobacillales or other beneficial gut microorganisms. Measurements can be made, as described in Example 10, via use of terminal restriction fragment length polymorphism (T-RFLP) analyses to identify the relative abundance of various microorganisms and assess the effect of the algal biomass regime.

IX. Dosage Forms

Administration of *Chlorella protothecoides* microalgal biomass in accordance with the methods of the present invention can be performed by providing to the patient or subject a microalgal biomass composition comprising an orally administrable dosage form. In some embodiments, the oral dosage form comprises a tablet or capsule, which may substitute for or supplement the subject's diet. In other embodiments, the oral dosage form comprises a food composition, which may be substituted for a portion of the subject's diet as a percentage by weight or by calories, or be used as a supplement.

A. Tablet and Capsule Formulations

In some cases, *Chlorella protothecoides* microalgal biomass can be manufactured into nutritional or dietary supplements. For example, *Chlorella protothecoides* biomass or oil extracted from the biomass can be encapsulated into digestible capsules in the manner similar to fiber capsules or fish oil. To prepare a tablet formulation for use in the methods of the present invention, *Chlorella protothecoides* microalgal biomass, can be encapsulated into digestible capsules, or compressed into a tablet by standard techniques familiar to those of skill in the art. In some cases, one or more excipients may be combined with the microalgal biomass in the capsule or tablet. Such capsules or tablets can be packaged in, e.g. a bottle or blister pack, and ingested on a daily basis or otherwise, as discussed in greater detail below with reference to administration schedules. In some cases, the tablet, capsule or other dosage formulation comprises a unit dose of biomass or algal oil.

Manufacturing of capsule and/or tablet dosage forms is preferably performed under GMP conditions appropriate for drug products (as codified at 21 CFR 210-211), nutritional supplements (as codified at 21 CFR 111), or comparable regulations established by jurisdictions outside the United States.

B. Food Product Formulations

Preparation of food compositions for use in the methods of the present invention comprise combining *Chlorella protothecoides* microalgal biomass, as described above, with at least one other edible ingredient, as described below, to form a food composition. In preferred embodiments, the preparatory methods are performed under GMP conditions appropriate for drug products (as codified at 21 CFR 210-211), food products (as codified at 21 CFR 110), or comparable regulations established by jurisdictions outside the United States.

In various embodiments, the food composition prepared for use in accordance with the methods of the invention comprises a baked good (e.g., cookies or a pie), a pasta product, a cake product, a bread product, an energy bar, a milk product, a juice product, or a smoothie. In various embodiments, the food composition weighs at least 10 g, at least 20 g, at least 30 g, at least 40 g, at least 50 g, at least 60 g, at least 70 g, at least 80 g, at least 90 g, at least 100 g, at least 200 g, at least 300 g, at least 400 g, or at least 500 g or more. In some embodiments, the food composition formed by the combination of *Chlorella protothecoides* microalgal biomass and at least one other edible ingredient is an uncooked product. In other cases, the food composition is a cooked product.

In some cases, the food composition formed by the combination of *Chlorella protothecoides* microalgal biomass and at least one other edible ingredient comprises at least 1.5%, at least 5%, at least 10%, at least 25%, or at least 50% w/w or v/v microalgal biomass. In some embodiments, food compositions formed as described herein comprise at least 2%, at least 3%, at least 4%, at least 15%, at least 20%, at least 30%, at least 35%, at least 40%, at least 45%, at least 55%, at least 60%, at least 65%, at least 70%, at least 75%, at least 80%, at least 85%, at least 90%, or at least 95% w/w microalgal biomass. In some cases, the food composition comprises 5-50%, 10-40%, or 15-35% algal biomass by weight or by volume.

In some cases, the food composition comprises predominantly intact *Chlorella protothecoides* microalgal cells. In some cases, the algal oil is predominantly encapsulated in cells of the biomass. In other cases, the biomass comprises predominantly lysed cells.

*Chlorella protothecoides* microalgal biomass can be combined with one or more other edible ingredients to make a food product. Alternatively, a manufacturer can sell *Chlorella protothecoides* microalgal biomass as a product, and a consumer can incorporate the algal biomass into a food product, for example, by modification of a conventional recipe. In either case, the algal biomass can be used to replace all or part of the oil, fat, eggs, or the like used in many conventional food products.

Other edible ingredients with which algal biomass can be combined in accordance with the present invention include, without limitation, grains, fruits, vegetables, proteins, meats, herbs, spices, carbohydrates, and fats. The other edible ingredients with which the *Chlorella protothecoides* microalgal biomass is combined to form food compositions depend on the food product to be produced and the desired taste, texture and other properties of the food product. In some food products, the microalgal biomass is combined with 2-20, 3-10, or 4-8 other edible ingredients. In some food products, the microalgal biomass is combined with at least 2, 3, 4, 5, 6, 7, 8, 9 or 10 other edible ingredients. The edible ingredients can be selected from all the major food groups, including without limitation, fruits, vegetables, legumes, meats, fish, grains (e.g., wheat, rice, oats, cornmeal, barley), herbs, spices, water, vegetable broth, juice, wine, and vinegar. In some food compositions, at least 2, 3, 4, or 5 food groups are represented as well as the algal biomass or algal oil.

In some embodiments, the food product formulations comprise at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% w/w or v/v *Chlorella protothecoides* microalgal biomass. Some food compositions comprise from 5-50%, 10-40%, or 15-35% microalgal biomass by weight or by volume. The remainder of a food composition in accordance with the present invention comprises other conventional edible ingredients, including those identified herein.

In cooked foods, the determination of percentages (i.e., weight or volume) can be made before or after cooking. The percentage of *Chlorella protothecoides* microalgal biomass can increase during the cooking process because of loss of liquids. Because *Chlorella protothecoides* microalgal biomass cells usually lyse in the course of the cooking process, it is difficult to measure the content of algal biomass directly in a cooked product. However, the content can be determined indirectly from the mass or volume of biomass that went into the raw product as a percentage of the weight or volume of the finished product.

In uncooked foods, most *Chlorella protothecoides* microalgal cells in the biomass remain intact. This has the advantage of protecting the algal oil from oxidation, which confers a long shelf-life. Depending on the nature of the food product, the protection conferred by the cells may reduce or avoid the need for refrigeration, vacuum packaging or the like. Retaining cells intact also prevents direct contact between the oil and the mouth of the subject administered the food product formulation. Alternatively, cells can be disrupted to release oil, which can provide the advantage of making the oil more available to perform a structural role in food preparation. Cells can be disrupted while in an aqueous suspension, which generally forms an emulsion, and also in dry form, which forms a free flowing powder of the cells are less than about 60% oil by dry cell weight.

Food compositions for use in accordance with the methods of the invention can include algal biomass with an oil content, an oil composition, and/or other constituents as described herein.

*Chlorella protothecoides* microalgal biomass for use in the methods of the present invention can also be formulated as a food ingredient, for combination with at least one other edible ingredient by a subject prior to ingestion. Such microalgal biomass is preferably manufactured and packaged under Good Manufacturing Practice (GMP) conditions for food products as codified at 21 C.F.R. 110. In these instances, the *Chlorella protothecoides* microalgal biomass can be packaged in an airtight container, such as a sealed bag. Optionally, the algal biomass can be packaged under vacuum to enhance shelf life. Refrigeration of packaged algal biomass is not required. The packaged *Chlorella protothecoides* microalgal biomass can contain instructions for use including directions for how to combine the algal biomass with at least one other edible ingredient to prepare a food composition for administration in accordance with the methods of the invention.

In some cases, *Chlorella protothecoides* microalgal biomass can be packaged in a form combined with other dry ingredients (e.g., sugar, flour, dry fruits, flavorings). The mixture can then be converted into a food product by a consumer by addition of at least one other edible ingredient. In some cases, a liquid can be added to reconstitute a dried algal biomass composition. Cooking can optionally be performed using a microwave oven, convection oven, or conventional oven. Such mixtures can be used for making cakes, breads, pancakes, waffles, drinks, sauces and the like. Such mixtures have advantages of convenience for the consumer as well as long shelf life without refrigeration. Such mixtures are typically packaged in a sealed container bearing instructions for adding liquid or other edible ingredients to convert the mixture into a food product for use in the methods of the invention.

In some cases, *Chlorella protothecoides* biomass can also be packaged as ready-to-mix material and presented in single use sachets or in bulk. Such ready-to-mix material can be combined with at least one other food product that is intended for human consumption. As a non-limiting example, *Chlorella protothecoides* biomass can be mixed with beverages such as water, juice, milk or other liquids. The *Chlorella protothecoides* biomass can also be mixed into food products such as yogurts.

X. Dose and Schedule of Administration

Effective doses of *Chlorella protothecoides* microalgal biomass can be administered to a patient as a single daily dose, or can be administered in a total daily dose divided into smaller doses administered two, three, four, or more times daily. In various embodiments, an effective dose of algal biomass comprises from 1 gram to 100 grams of biomass per day. In some cases, an effective dose comprises from 1 gram to 250 grams per day. In some cases, an effective dose of algal biomass comprises from 1-5 grams of biomass per day. In some cases, an effective dose comprises from 1-10 grams, from 5-20 grams, from 10-50 grams, from 20-75 grams, or from 25-100 grams of biomass per day. In some embodiments, an effective dose of algal biomass in accordance with the methods of the present invention comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 grams of biomass per day. In some cases, the effective dose comprises at least the amount identified in any one of the doses or dosage ranges discussed above.

In some cases, an effective dose comprises from 1-2 grams of *Chlorella protothecoides* microalgal biomass per day. In other cases, an effective dose comprises from 1.5-2.5, or from 2-3 grams of algal biomass per day. In still other cases, the effective dose is at least 1 g, at least 1.5 g, at least 1.75 g, at least 2 g, at least 2.25 g, at least 2.5 g, at least 2.75 g, or at least 3 g of algal biomass per day.

In some cases, the dose of *Chlorella protothecoides* microalgal biomass comprises a defined percentage of the patient's diet by weight or calories. In various embodiments, the percentage may range from 1-20%, from 2-15%, from 3-10%, from 2.5-5%, or the like. In some cases, the daily dose of algal biomass comprises 1%, 1.5% 2%, 2.5%, 3%, 3.5%, 4%, 4.5%, 5%, 5.5% 6%, 6.5%, 7%, 7.5%, 8%, 8.5%, 9%, 9.5%, 10%, 11%, 12%, 13%, 14%, 15%, 16%, 17%, 18%, 19%, or 20% of the patient's daily diet by weight or by calories.

Administration of *Chlorella protothecoides* microalgal biomass to a patient can be performed according to a particular treatment schedule or dosing regimen. In some cases, *Chlorella protothecoides* microalgal biomass is administered daily for at least one week, at least two weeks, at least three weeks, at least four weeks, at least one month, at least two months, at least three months, at least six months, at least nine months, at least one year, at least two years, at least five years, or for life.

In some cases, administration of a daily dose of *Chlorella protothecoides* microalgal biomass is proximate in time to intake of a meal. In these instances, administration of algal biomass with at least one other edible ingredient in a food composition may be convenient for the patient.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

Although this invention has been described in connection with specific embodiments thereof, it will be understood that it is capable of further modifications. This application is intended to cover any variations, uses, or adaptations of the use of *Chlorella protothecoides* microalgal biomass following, in general, the principles of the invention and including such departures from the present disclosure as come within known or customary practice within the art to which the invention pertains and as may be applied to the essential features hereinbefore set forth.

XI. EXAMPLES

The following examples are offered to illustrate, but not to limit, the claimed invention.

Example 1

*Chlorella protothecoides* strains from the University of Texas culture collection were tested for growth on glycerol and glucose (UTEX 31, 249, 250, 264). Each strain was inoculated from solid media into 25 ml liquid base media (2 g/L yeast extract, 2.94 mM $NaNO_3$, 0.17 mM $CaCl_2.2H_2O$, 0.3 mM $MgSO_4.7H_2O$, 0.4 mM $K_2HPO_4$, 1.28 mM $KH_2PO_4$, 0.43 mM NaCl) and grown shaking at 27° C. for 72 hours under a light intensity of 75 $\mu Em^{-2}s^{-1}$. These cultures were used to inoculate each strain to a final density of $1\times10^5$ cells per ml into 24-well plates containing 2 ml of (a) base media only; (b) base media plus 0.1% glucose; and (c) base media plus 0.5% reagent grade glycerol (EM Science, catalog #GX0185-6). Plates were placed in the dark and grown for 72 hours shaking at 27° C. Samples of each strain grown in the three conditions were diluted 1.9:1 in distilled $H_2O$ and absorbance was read at 600 nm in a Molecular Devices SpectraMax 340PC. All strains exhibited growth in the presence of glucose and glycerol compared to only base media.

Example 2

Strains and Media: *Chlorella protothecoides* (STRAIN 250), (STRAIN 249), and (STRAIN 31) were obtained from the Culture Collection of Alga at the University of Texas (Austin, Tex., USA). The stock cultures were maintained on modified Proteose medium. Modified Proteose medium consisted (g/L) of 0.25 g $NaNO_3$, 0.09 g $K_2HPO_4$, 0.175 g $KH_2PO_4$, 0.025 g $CaCl_2.2H_2O$), 0.075 g $MgSO_4.7H_2O$ and 2 g yeast extract per liter. Glycerol wastes from biodiesel production (acidulated glycerol (AG) and non-acidulated glycerol (NAG)) were obtained from Imperial Western Products (Selma, Calif., USA). "Pure" or "reagent grade" glycerol was from EM Science (a division of Merck KGA), catalog #GX0185-6.

Experimental design and lipid assay: For each strain, 1 ml of following different media was prepared in 24-well plates.
1. Proteose+1% pure glycerol+1% glucose
2. Proteose+1% pure glycerol+1% glucose (added after 72 hr)
3. Proteose+1% acidulated glycerol+1% glucose
4. Proteose+1% acidulated glycerol+1% glucose (added after 72 hr)
5. Proteose+1% non acidulated glycerol+1% glucose
6. Proteose+1% non acidulated glycerol+1% glucose (added after 72 hr)

Each strain was inoculated to different media to $5\times10^5$ cells/ml concentration. The cultures were kept in dark and agitated by orbital shaker from Labnet (Berkshire, UK) at 430 rpm. After 72 hr of initial growth, 1% (w/v) glucose was added to #2, #4, and #6 media and cultured another 24 hr. Dried cell-weight was measured in all samples. To measure dry cell weight, 1 ml of each culture was pelleted by centrifugation at 5,000 rpm for 5 minutes in an Eppendorf 5415C centrifuge. After removing supernatant, cell pellets were frozen at −80° C. and lyophilized in a lab scale freeze dryer (Labconco, Mo., USA). After the cell pellets are dried, their weight was determined. Results are shown in FIG. 1.

Example 3

Strains and Media:

*Chlorella protothecoides* (UTEX 31) was obtained from the Culture Collection of Algae at the University of Texas (Austin, Tex., USA). The stock cultures were maintained on modified Proteose medium (see EXAMPLE 2).

Experimental Design:

For each condition, 1 ml of following different media was prepared in 24-well plates.

4. Proteose
5. Proteose+0.5% glucose
6. Proteose+0.5% xylose
7. Proteose+0.25% glucose+0.25% xylose

*Chlorella protothecoides* (UTEX 31) was inoculated to media containing different sugars (glucose, or xylose) to $3 \times 10^5$ cells/ml concentration. The cultures were kept in dark and agitated by orbital shaker from Labnet (Berkshire, UK) at 430 rpm. After 72 hr of growth, cell growth was measured by counting cell numbers of each culture. Results are shown in FIG. 2.

Example 4

*Chlorella protothecoides* strains (UTEX 250), (UTEX 249) and (UTEX 31)) were obtained from the Culture Collection of Algae at the University of Texas (Austin, Tex., USA). The stock cultures were maintained on modified Proteose medium (see EXAMPLE 2). For each condition, 1 ml of following different media was prepared in 24-well plates.

1. Proteose
2. Proteose+1% glucose
3. Proteose+1% fructose

Figure 3:
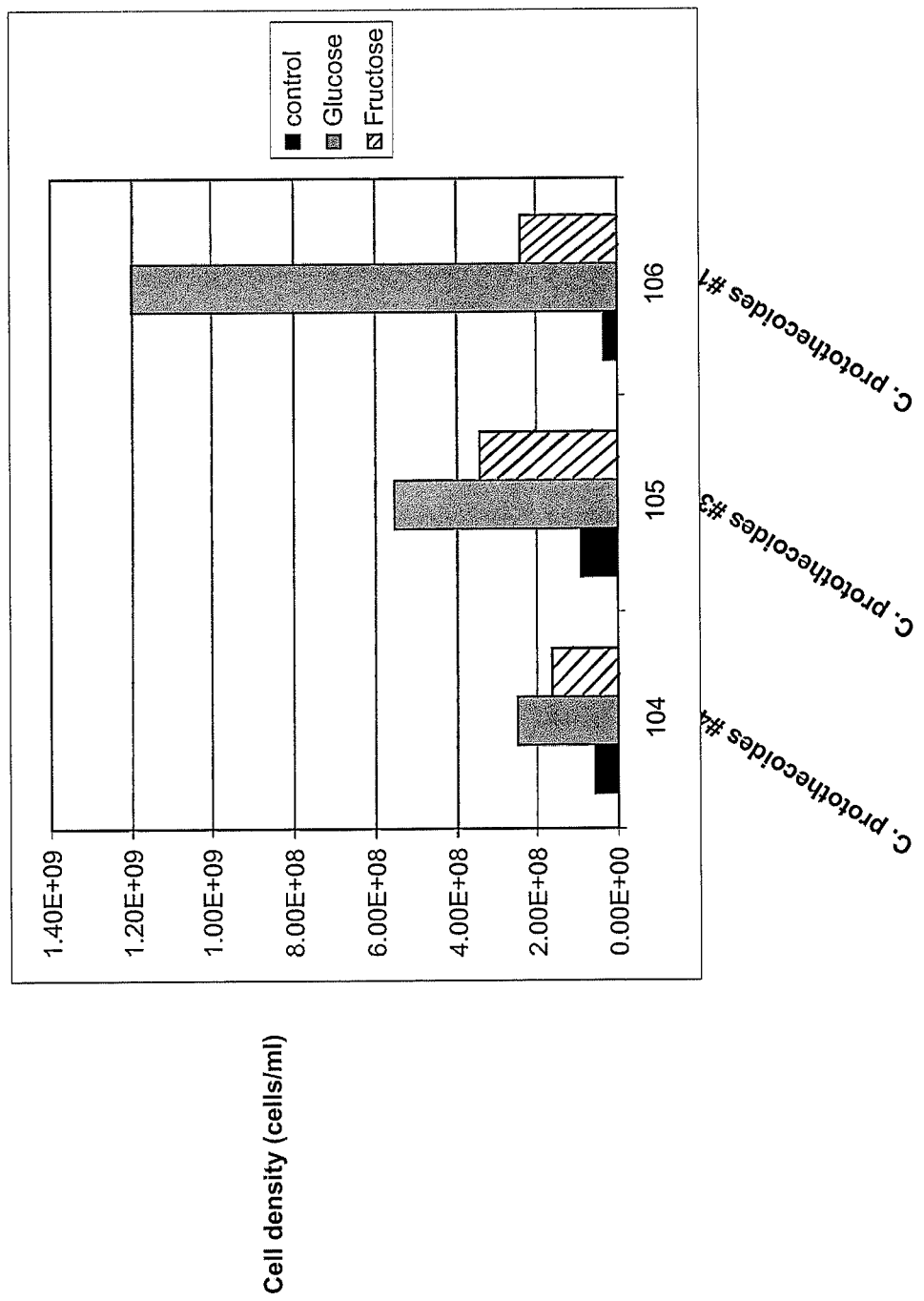
FIG. 3 shows growth of *Chlorella protothecoides* on glucose and fructose.

Each strain was inoculated to media containing different sugars (glucose, or fructose) to $1 \times 10^6$ cells/ml concentration. The cultures were kept in dark and agitated by orbital shaker from Labnet (Berkshire, UK) at 430 rpm. After 96 hr of growth, cell density was measured by counting cell numbers of each culture. Results are shown in FIG. 3.

Example 5

*Chlorella* on Sucrose

Materials and Methods:

*Chlorella protothecoides* (UTEX 249) was inoculated into three 50 ml flasks of Proteose media with 1% sucrose (2.94 mM NaNO$_3$, 0.428 mM K$_2$HPO$_4$, 1.28 mM KH$_2$PO$_4$, 0.427 mM NaCl, 0.17 mM CaCl$_2$-2H$_2$O, 0.3 mM MgSO$_4$-7H$_2$O, proteose peptone 1 g/L) to a final cell density of $4 \times 10^5$ cells per ml. Invertase (Sigma #I4504) was added to two of the cultures at 0.01 U/ml and 0.05 U/ml. All three cultures were grown in the dark for ~60 hrs shaking at 150 rpm.

Results:

Final cell counts were performed on all three cultures after ~60 hrs of shaking in the dark. The control flask reached $4.4 \times 10^5$ cells per ml while the 0.01 U/ml and 0.05 U/ml flasks reached cell densities of $1 \times 10^8$ and $3 \times 10^8$ respectively. Each flask was checked for contamination at the end of the experiment by microscopic analysis and all were clean.

Example 6

Carbon Utilization Screens

Strains and Culture Conditions:

Seed cultures of the various strains of *Chlorella protothecoides* identified below were started as 1 ml liquid cultures in 24 well plates and were grown autotrophically for 48 hours in light, agitating at ~350 rpm. Plates were setup with 1.5% agarose-based solid Proteose media (see EXAMPLE 2) containing 1% of glucose, glycerol, xylose, sucrose, fructose, arabinose, mannose, galactose, or acetate as the sole fixed carbon source. For each strain, 5 µl of culture from the autotrophic 24 well plate was spotted onto the solid media. Plates were incubated for 7 days in the dark at 28° C. and examined for growth compared to a control plate containing no additional fixed carbon. Growth was observed for each of the species tested with each respective feedstock, as shown in Table 2 below. Growth of these strains on Proteose media in the dark in the absence of additional fixed carbon either did not occur or was extremely minimal

TABLE 2

*Chlorella protothecoides* grown on various fixed-carbon feedstocks.

| Fixed Carbon Source | Genus/Species | Source/Designation |
|---|---|---|
| Glucose | *Chlorella protothecoides* | UTEX 250 |
| Glycerol | *Chlorella protothecoides* | CCAP 211/8d |
| Fructose | *Chlorella protothecoides* | UTEX 31 |
| Fructose | *Chlorella protothecoides* | UTEX 250 |
| Fructose | *Chlorella protothecoides* | CCAP 211/8d |
| Mannose | *Chlorella protothecoides* | UTEX 250 |
| Galactose | *Chlorella protothecoides* | UTEX 25 |
| Galactose | *Chlorella protothecoides* | UTEX 250 |
| Galactose | *Chlorella protothecoides* | UTEX 264 |
| Acetate | *Chlorella protothecoides* | UTEX 31 |
| Acetate | *Chlorella protothecoides* | UTEX 411 |
| Acetate | *Chlorella protothecoides* | CCAP 211/8d |
| Acetate | *Chlorella protothecoides* | UTEX 250 |

Example 7

Preparation of Biomass

Microalgal biomass is generated by culturing microalgae as described in any one of Examples 1-6 or through methods described herein such as Miao and Wu, *J. Biotechnology*, 2004, 11:85-93. The microalgal biomass is then harvested from the culture bioreactor, and washed with water to remove residual salts and culture media.

GMP procedures are followed. Any person who, by medical examination or supervisory observation, is shown to have, or appears to have, an illness, open lesion, including boils, sores, or infected wounds, or any other abnormal source of microbial contamination by which there is a reasonable possibility of food, food-contact surfaces, or food packaging materials becoming contaminated, is to be excluded from any operations which may be expected to result in such contamination until the condition is corrected. Personnel are instructed to report such health conditions to their supervisors. All persons working in direct contact with the microbial biomass, biomass-contact surfaces, and biomass-packaging materials conform to hygienic practices while on duty to the extent necessary to protect against contamination of the microalgal biomass. The methods for maintaining cleanliness include, but are not limited to: (1) wearing outer garments suitable to the operation in a manner that protects against the contamination of biomass, biomass-contact surfaces, or biomass packaging materials; (2) maintaining adequate personal cleanliness; (3) washing hands thoroughly (and sanitizing if necessary to protect against contamination with undesirable microorganisms) in an adequate hand-washing facility before starting work, after each absence from the work station, and at any other time when the hands may have become soiled or contaminated; (4) removing all unsecured jewelry and other objects that might fall into biomass, equipment, or containers, and removing hand jewelry that cannot be adequately sanitized during periods in which biomass is manipulated by hand. If such hand jewelry cannot be removed, it maybe covered by material which can be maintained in an intact, clean, and sanitary condition and which effectively protects against the contamination by these objects of the biomass, biomass-contact surfaces, or biomass-packaging materials; (5) maintaining gloves, if they are used in biomass handling, in an intact, clean and sanitary condition. The gloves should be of an impermeable material; (6) wearing, where appropriate, in an effective manner, hair nets, headbands, caps, beard covers, or other effective hair restraints; (7) storing clothing or other personal belongings in areas other than where biomass is exposed or where equipment or utensils are washed; (8) confining the following to areas other than where biomass may be exposed or where equipment or utensils are washed: eating foodstuffs, chewing gum, drinking beverages, or using tobacco; (9) taking any other necessary precautions to protect against contamination of biomass, biomass-contact surfaces, or biomass-packaging materials with microorganisms or foreign substances including, but not limited to, perspiration, hair, cosmetics, tobacco, chemicals, and medicines applied to the skin. The microbial biomass can optionally be subjected to a cell disruption procedure to generate a lysate and/or optionally dried to form a microalgal biomass composition.

The microalgal biomass can optionally be subjected to a cell disruption procedure to generate a lysate and/or optionally dried to form a microalgal biomass composition. A variety of methods of cell disruption can be suitable including chemical, thermal, mechanical, mills, ultrasonication, homogenization or combinations thereof.

Example 8

Lipid Profile of *Chlorella protothecoides*

Growth:

Cultures of *Chlorella protothecoides* obtained from the Culture Collection of Algae at the University of Texas (Austin, Tex., USA), were maintained and all experiments were carried out in Modified Protease media (see EXAMPLE 2). For each strain, 10 ml cultures were setup in 50 ml flasks as follows:
1. Protease growth media with no carbon addition;
2. Protease growth media with 1% glucose.

*Chlorella protothecoides* was grown in the two conditions described above, at an initial seeding density of $1.0 \times 10^6$ cells/ml. The cultures were kept in the dark and agitated at 250 rpm for 7 days. The cells were harvested after a 7 day growth period, and assessed for growth in the dark relative to the control by measuring dried cell weight. Dry cell weights were determined as follows: One ml of culture was centrifuged and the resulting pellet was rinsed with water to remove any salt or residual media; the final, rinsed pellet was frozen at −80 degree C.; and subjected to freeze drying overnight in a Freeze Dry System (Labconco, Mo., USA). Glycerolipid profile was determined by HPLC analysis: Approximately 10 mg of dried biomass was mixed with 1 ml of isopropanol saturated with KOH and incubated at 80° C. for 4 hours. Lipids from cell pellets were extracted and hydrolyzed using an isopropanol potassium hydroxide solution heated to 80° C. for four hours. The extract samples were analyzed with an Agilent 1100 HPLC using the following method. The samples were derivatized with bromophenacyl bromide (60 mg/ml) and loaded onto a Luna 5 u C8(2) 100 A 150×2 mm column (Phenomenex). The samples were eluted from the column using a gradient of water to 100% Acetonitrile:tetrahydrofuran (95:5). Signals were detected using DAD array detector at a wavelength of 254 nm. The results are expressed as a percentage of total lipids and are summarized below in Table 3.

TABLE 3

| Glycerolipid profiles of *Chlorella protothecoides*. | | | | | | | | | |
|---|---|---|---|---|---|---|---|---|---|
| Species | C 14:0 | C 16:0 | C 16:1 | C 18:0 | C 18:1 | C 18:2 | C 18:3 | C 20:0 | C 20:1 |
| *Chlorella protothecoides* (UTEX 250) | 0.57 | 10.30 | 0 | 3.77 | 70.52 | 14.24 | 1.45 | 0.27 | 0 |
| *Chlorella protothecoides* (UTEX 25) | 0.61 | 8.70 | 0.30 | 2.42 | 71.98 | 14.21 | 1.15 | 0.20 | 0.24 |

Example 9

Reduction of Plasma Glucose Levels and Body Weight via Algal Biomass Administration Methods:

An F-Tank batch of *Chlorella protothecoides* (UTEX 250) (about 1,200 gallons) was used to generate biomass. The batch (#ZA07126) was allowed to run for 100 hours, while controlling the glucose levels at 16 g/L, after which time the corn syrup feed was terminated. Residual glucose levels dropped to <0 g/L two hours later. This resulted in a final age of 102 hours. The final broth volume was 1,120 gallons. Both in-process contamination checks and a thorough analysis of a final broth sample failed to show any signs of contamination. The fermentation broth was centrifuged and drum dried.

Forty five Syrian golden hamsters (*Mesocricetus auratus*; n=15 per group) were randomized to receive either control hypercholesterolemia inducing diet alone, or the same diet with added *Chlorella protothecoides* biomass that contained intact (undisrupted) cells. The *Chlorella protothecoides* biomass contained 22% lipid dry cell weight and was added to the diet as a dried powder. The compositions of the diets are shown in Table 4 below. All animals were then fed the hypercholesterolemia inducing diet ad libitum for 28 days with body weight and food consumption measured every three days. On day 25, energy expenditure, expressed as oxygen consumption per gram body weight, was measured by indirect calorimetry using a respiratory gas exchange system for rodents (MM-100 CWE, Inc. Pennsylvania, USA) Animals were then euthanized with an overdose of sodium pentobarbital; body composition was determined immediately by dual emission x-ray absorptiometry (DEXA). The study protocol was approved by the University of Manitoba Animal Care Committee in accordance to the Canadian Council on Animal Care Guidelines.

TABLE 4

Composition of hypercholesterolemia diets.
Diet compositions (g/kg dry matter)

| Ingredients | Control Diet | 2.5% C. Protothecoides | 5.0% C. Protothecoides |
|---|---|---|---|
| Casein | 200 | 200 | 200 |
| Corn starch | 260 | 235 | 210 |
| Sucrose | 330 | 330 | 330 |
| Lard/Sunflower Mix | 50 | 50 | 50 |
| Cellulose | 105 | 105 | 105 |
| DL-methionine | 5 | 5 | 5 |
| Mineral mixture | 35 | 35 | 35 |
| Vitamin mixture | 10 | 10 | 10 |
| Choline bitartrate | 2 | 2 | 2 |
| BTH | 0.2 | 0.2 | 0.2 |
| Cholesterol | 2.5 | 2.5 | 2.5 |
| Test Article | 0 | 25 | 50 |
| Total | 1000 | 1000 | 1000 |

Blood was collected in heparinized tubes and separated into plasma and packed red blood cells by centrifugation. Plasma glucose, triglycerides, total cholesterol and HDL cholesterol were measured using the Vitros Chemistry System 350 (Ortho-Clinical Diagnostics, Johnson and Johnson, USA). Plasma insulin was measured by ELISA assay (Millipore, Mo., USA) using 10 μL of sample.

Results:

Table 5, below, shows the results of the physiological, biochemical, and percentage body fat measurements obtained from the Syrian golden hamsters administered the hyperglycemia-inducing diets with or without algal biomass, as shown in Table 4.

TABLE 5

Physiological, biochemical and % body fat measurements.

| | | P vs. Control |
|---|---|---|
| % Body Fat (% Total) | | |
| Control | 52.4 ± 1.3 | |
| 2.5% Chlorella protothecoides | 50.5 ± 1.4 | NS |
| 5.0% Chlorella protothecoides | 48.3 ± 1.6 | 0.06 |
| Oxygen Consumption (ml/g LBM) | | |
| Control | 1.56 ± 0.09 | |
| 2.5% Chlorella protothecoides | 2.20 ± 0.27 | 0.03 |
| 5.0% Chlorella protothecoides | 2.12 ± 0.26 | 0.05 |
| Carbon Dioxide Production (ml/g LBM) | | |
| Control | 1.02 ± 0.06 | |
| 2.5% Chlorella protothecoides | 1.09 ± 0.09 | NS |
| 5.0% Chlorella protothecoides | 1.03 ± 0.08 | NS |
| Total Plasma Protein (g/L) | | |
| Control | 64.9 ± 1.5 | |
| 2.5% Chlorella protothecoides | 65.0 ± 1.1 | NS |
| 5.0% Chlorella protothecoides | 63.7 ± 1.1 | NS |

TABLE 5-continued

Physiological, biochemical and % body fat measurements.

| | | P vs. Control |
|---|---|---|
| Plasma Albumin (g/L) | | |
| Control | 32.0 ± 0.8 | |
| 2.5% Chlorella protothecoides | 32.3 ± 0.6 | NS |
| 5.0% Chlorella protothecoides | 31.3 ± 0.7 | NS |

Figure 4:
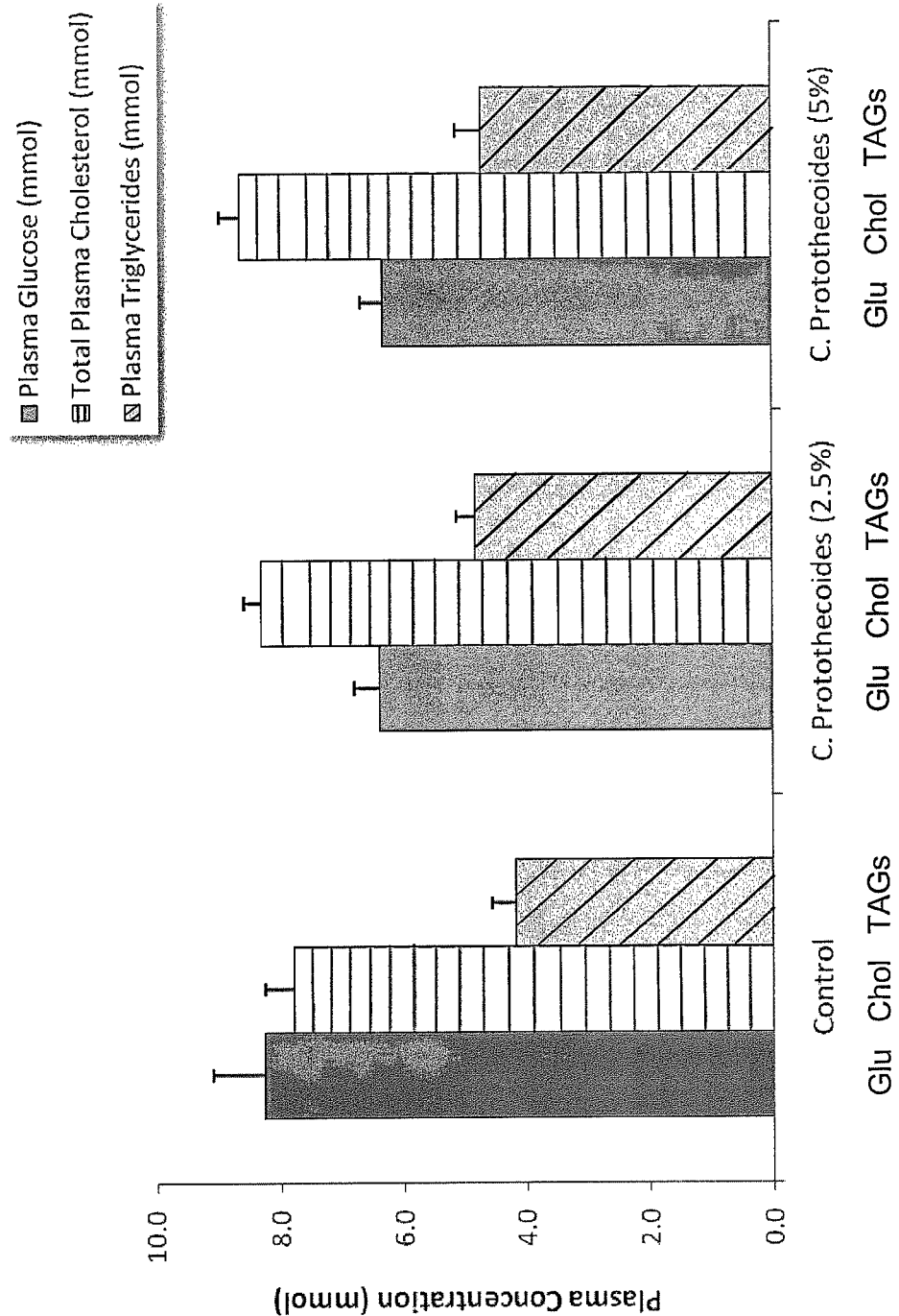
FIG. 4 shows plasma glucose, cholesterol and triglyceride concentrations in Syrian golden hamsters that had consumed a hyperglycemia-inducing diet with and without algal biomass from cultured *Chlorella protothecoides*. Values are mean±SEM and bars with differing letter superscripts are different from one another at $P<0.05$ (one-way ANOVA).
Figure 5:
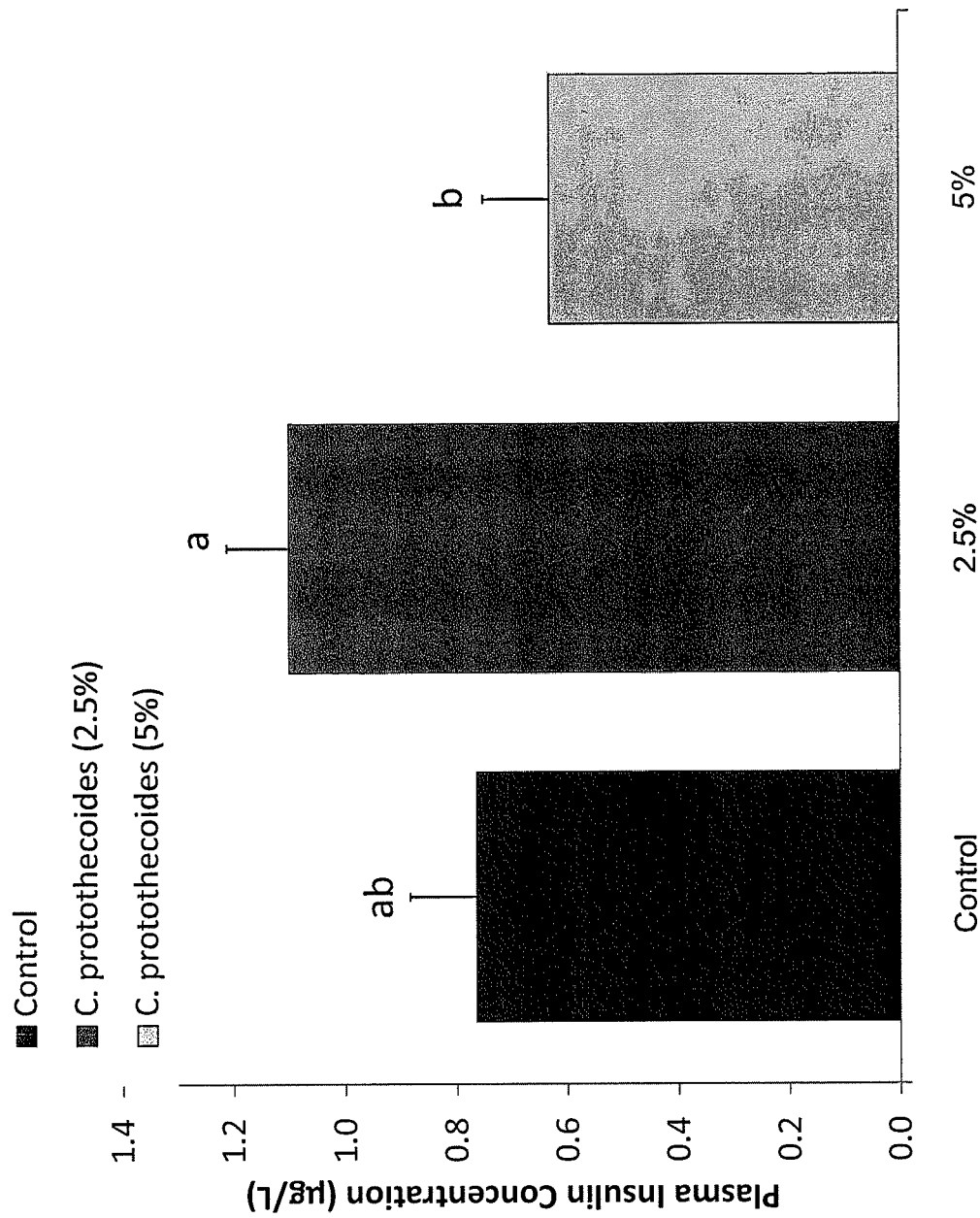
FIG. 5 shows plasma insulin concentrations in Syrian golden hamsters that had consumed a hyperglycemia-inducing diet with and without algal biomass from cultured *Chlorella protothecoides*. Values are mean±SEM and differing letters indicate difference at $P<0.05$ (one-way ANOVA).
Figure 6:
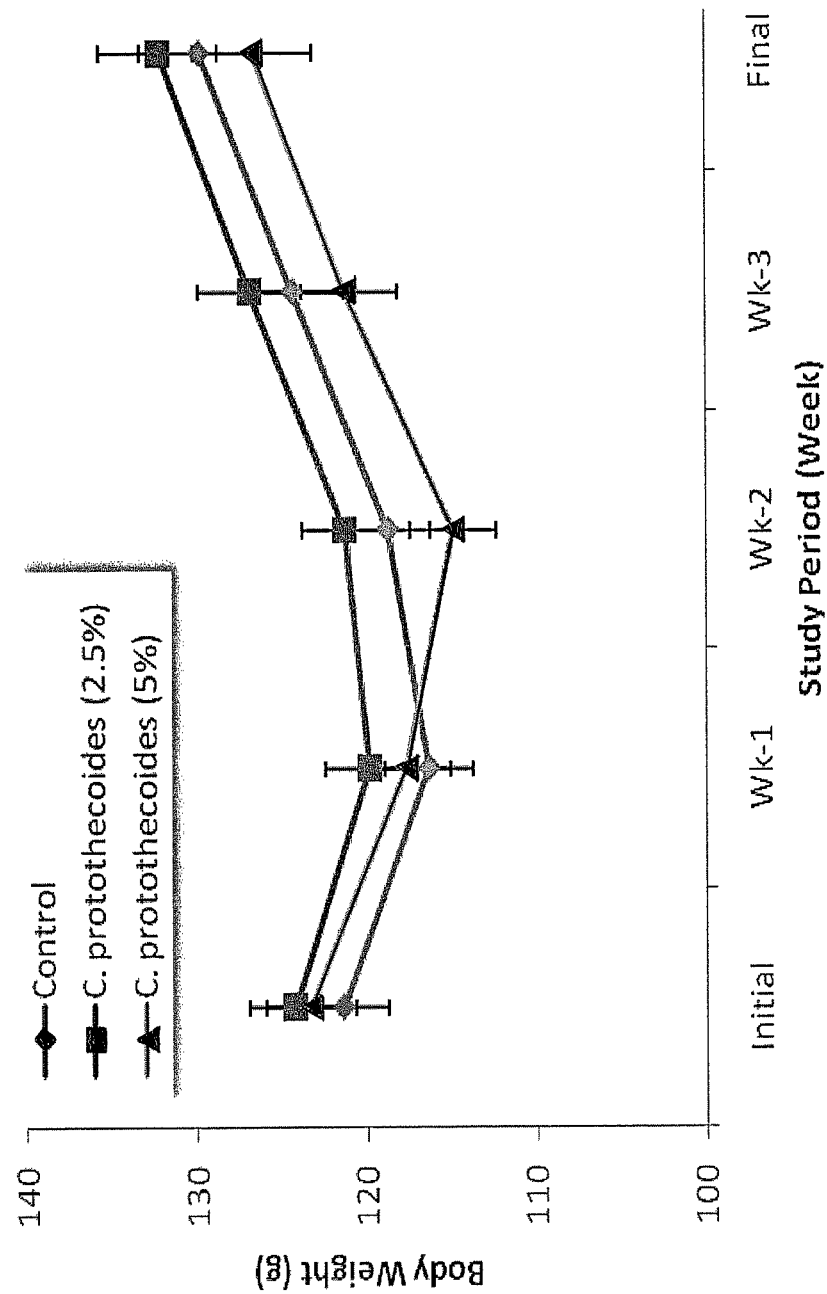
FIG. 6 shows body weight of Syrian golden hamsters that had consumed a hyperglycemia-inducing diet with and without algal biomass from cultured *Chlorella protothecoides*. Values are mean±SEM and body weight gain was not significantly different between groups (repeated measures ANOVA).

Consumption of C. protothecoides in a semi-purified hypercholesterolemic and hyperglycaemic-inducing diet decreased plasma glucose independent of insulin concentrations in the Syrian golden hamster model. In particular, the data show that incorporation of C. protothecoides into a hyperglycaemic dietary matrix improves insulin sensitivity, as illustrated by the 25% reduction in plasma glucose (see FIG. 4, P<0.05), without increasing circulating insulin concentrations (see FIG. 5, P>0.05) in the Syrian golden hamster. The data also show that consuming C. protothecoides in a food matrix exerts an effect on energy expenditure through an increase in $O_2$ consumption without changing $CO_2$ production (see Table 5). Body weight gain was not different between groups (see FIG. 6) but the consumption of C. protothecoides at 5% tended to reduce % total body fat (see Table 5, P=0.06), a finding which is also linked to better glycemic control. The consumption of C. protothecoides at 2.5% and 5% of total diet (w/w) did not result in any difference between groups in the liver production of total plasma protein or albumin, the former usually modestly increased or decreased in stress situations and the latter decreased in acute inflammation responses (see Table 5). Consumption of this relatively high lipid biomass did not affect blood lipids as compared to controls (see FIG. 4, P>0.05).

Chlorella protothecoides biomass, added to a food matrix, lowered blood glucose levels by 25% in Syrian golden hamsters compared to controls consuming the same diet without added algal biomass. The percentage body fat tended to decrease with C. protothecoides consumption while $O_2$ utilization tended to increase with C. protothecoides consumption, indicating possible changes in preferred energy substrate and metabolic rate.

Example 10

Increased Relative Abundance of Beneficial Gut Microflora via Algal Biomass Consumption Methods:

Forty five Syrian golden hamsters (Mesocricetus auratus; n=15 per group) were randomized to receive either control hypercholesterolemia inducing diet alone, or the same diet with added Chlorella protothecoides biomass of the same lot used to formulate diets in Example 9, formulated as shown in Table 4 above. All animals were then fed the hypercholesterolemia inducing diet ad libitum for 28 days. On day 28, after the animals were euthanized by overdose with sodium pentobarbital, caecums were removed and immediately frozen in liquid nitrogen and stored at −80° C. until analyzed.

Terminal restriction fragment length polymorphism (T-RFLP) analysis was carried out on the pooled contents of four caecums randomly selected from the fifteen caecums stored for each group, and the results cross-referenced with known DNA sequences form 16s rDNA clones. The results are summarized in Table 6 below.

T-RFLP uses natural variation in the 16s rDNA to classify the composition of a complex microbial microsystem in a hierarchal manner from phylum→class→order. Genomic DNA extraction from mycobacterium has been described in the art and can be suitable for extraction of DNA for T-RFLP. DNA extraction for the caecum samples was performed according to the methods described in Kotlowski, et al., *J. Med. Microbio.* (2004) 53: 927-933. Primers 27f (forward) 5'-GAAGAGTTTGATCATGGCTCAG-3' (SEQ ID NO:1) and 342r (reverse) 5'-CTGCTGCCTCCCGTAG-3' (SEQ ID NO:2) were used in order to amplify part of the 16S rDNA gene. The forward primer were fluorescently labeled (Well-RED D4dye, Sigma-Proligo, St. Louis, Mo.) to allow detection of the fragments by capillary electrophoresis. The polymerase chain reaction (PCR) was performed as follows: 94° C. for 1 minute; 36 cycles at 94° C. for 1 minute; 55° C. for 1 minute; 72° C. for 2 minutes; and a final extension at 72° C. for 5 minutes.

Following the PCR amplification, the samples were subjected to restriction enzyme digestion in order to produce terminal restriction fragments; the 27-342 region of 16S DNA was digested using HhaI (10 µl of PCR product, 10 unites of HhaI, 1× HhaI buffer and 20 µg of bovin serum). The mix was adjusted to a final volume of 20 µl with MilliQ (Millipore, Bedford, Mass.) water and the DNA was digested at 37° C. for 3 hours. The precise length of terminal restriction fragments were determined by performing capillary electrophoresis with a CEQ 8800 Genetic Analysis System (Beckman Coulter, Fullerton, Calif.). 2 µl of fluorescently labeled fragments (from the restriction digests), 26 µl of sample loading solution, and 0.5 µl of DNA size standard (400 bp) were mixed and separated using capillary electrophoresis. An electropherogram with peaks of different sizes was obtained for each sample. Each peak represented an operational taxonomic unit (OTU) and was identified by its fragment size. However, the data produced from the specific DNA sequence does not always correspond to a known or culturable microbial species. Therefore, this particular analysis allows for qualitative or semiquantitative description of microbial populations. Along with the changes in phylogenetic diversity, the actual number of matches in the Ribosomal Database Project II (accession number) also gives an indication of the diversity, as the total number of matches in the database indicates a uniquely cloned terminal fragment. See Ribosomal Database Project (RDP), Center for Microbial Ecology at Michigan State University; accessed on Jul. 23, 2008 at http://rdp.cme.msu.edu/index.jsp. Changes greater than or equal to 2 fold are generally considered biologically significant. Similar analytical techniques have been described in Sepehri et al., *Inflamm Bowel Dis* (2007), 13(6): 675-683 and are hereby incorporated by reference for all purposes.

Results:

Table 6 shows the relative changes in caecal microflora in response to ingestion of *C. protothecoides* biomass, as described above. Relative changes were calculated by setting the control group hamster data as the 100% and measuring the relative fold changes for the 2.5% and 5.0% *C. protothecoides* groups. The greater than 5 fold change in the class Lactobacillales compared to control hamsters indicates a positive and healthy change in gut microflora. Generally regarded as healthy, bacteria from the class Lactobacillales are normally found in fermented dairy products. More recently, the food industry has started to include various species (single or in combination) from this particular order in food preparation under the functional food category "probiotics". Therefore, a "prebiotic" capable of inducing the greater than 5 fold changes in favour of this particular species, in vivo, is significant, especially given the absence of these bacteria in the diet.

Other noteworthy changes include a different microbial pattern for class Gammaproteobacteria. Specifically, control animals had higher relative numbers from the order Pasteurellales, which contains normal gut commensal bacterial species to pathogenic species, such as *Haemophilus influenza*, which is known to cause infection like pneumonia and bacterial meningitis. The consumption of 2.5% and 5.0% *C. protothecoides* also resulted in a greater than 2 fold increase in class Enterobacteriales, which includes *Escherichia coli*. Members of this particular class are commonly found in the intestinal microflora. Other changes included differences in the class Clostridia. Finally, a 7 fold increase in the class Lentisphaerae was noted in the 2.5% *C. protothecoides* hamsters, while the class was not detected in the control or 5% *C. protothecoides*.

These data support the conclusion that algal biomass comprising significant quantities of algal oil (e.g., at least 15%) acts as a prebiotic for Lactobacillales species, and that consumption of such algal biomass increases the relative size of this population in the gut.

TABLE 6

Relative changes in caecal micorflora.

| Bacterial Classification | Control | 2.5% C. protothecoides | 5.0% C. protothecoides |
| --- | --- | --- | --- |
| Total Accession Numbers* | 71 (1) | 149 (2.1) | 127 (1.8) |
| phylum *Lentisphaerae* | none detected | 7 | none detected |
| class *Lentisphaerae* | none detected | 7 | none detected |
| phylum *Firmicutes* | 1 | 1 | 1 |
| class *Bacilli* | 1 | 5.3 | 5.6 |
| order *Lactobacillales* | 1 | 5.3 | 5.6 |
| class *Clostridia* | 1 | 0.94 | 0.92 |
| order *Clostridiales* | 1 | 0.82 | 0.89 |
| unclassified *Clostridia* | 1 | 4.8 | 1.8 |
| phylum *Proteobacteria* | 1 | 0.96 | 1.1 |
| class Gammaproteobacteria | 1 | 2.4 | 2.8 |
| order *Pasteurellales* | 1 | 0.50 | 0.57 |
| order *Enterobacteriales* | none detected | 2.7 | 3.1 |
| unclassified Proteobacteria | none detected | 7 | 8 |

*Total accession numbers refers to the total number of unique matches in the RDP II database. This value is also reflective of the change in diversity for the microbial population of the caecum.

Example 11

Formulation of *Chlorella protothecoides* Biomass Suitable for Human Consumption

*Chlorella protothecoides* biomass is prepared under conditions described above in Example 7. The biomass can be formulated in an encapsulated form or as a tablet that is suitable for human consumption. Biomass formulated in an encapsulated form or as a tablet ideally should be manufactured under GMP conditions appropriate for nutritional supplements as codified at 21 C.F.R. 111, or comparable regulations established by foreign jurisdictions. The dried *Chlorella protothecoides* biomass can also be mixed in with foods such as yogurt, breakfast cereal, salads, salad dressings, etc. or in beverages such as shakes, juice drinks or smoothies. The biomass should be taken at a level where increased probiotic levels can be observed.

Example 12

Genotyping of *Chlorella protothecoides*

Genomic DNA was isolated from the following *Chlorella protothecoides* strains: UTEX 25, UTEX 249, UTEX 250, UTEX 256, UTEX 264, UTEX 411, CCAP 211/17 and CCAP 211/8d. Cells (approximately 200 mg each) were centrifuged from liquid cultures for 5 minutes at 14,000×g. Cells were then resuspended in sterile distilled water, centrifuged for 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25M Sucrose, 50 mM NaCl, 20 mM EDTA, 100 mM Tris-HCl, pH 8.0, 0.5 µg/µl RNase A) was added. Pellets were resuspended by vortexing briefly, followed by the addition of 40 µl of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatants were transferred to fresh tubes and extracted once with 300 µl Phenol:Chloroform:Isoamyl alcohol 12:12, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Figure 7A:
FIGS. 7*a-c* show a 23S rRNA genomic sequence analysis of strains designated as *Chlorella protothecoides*, as described in the Examples below.
Figure 7B:
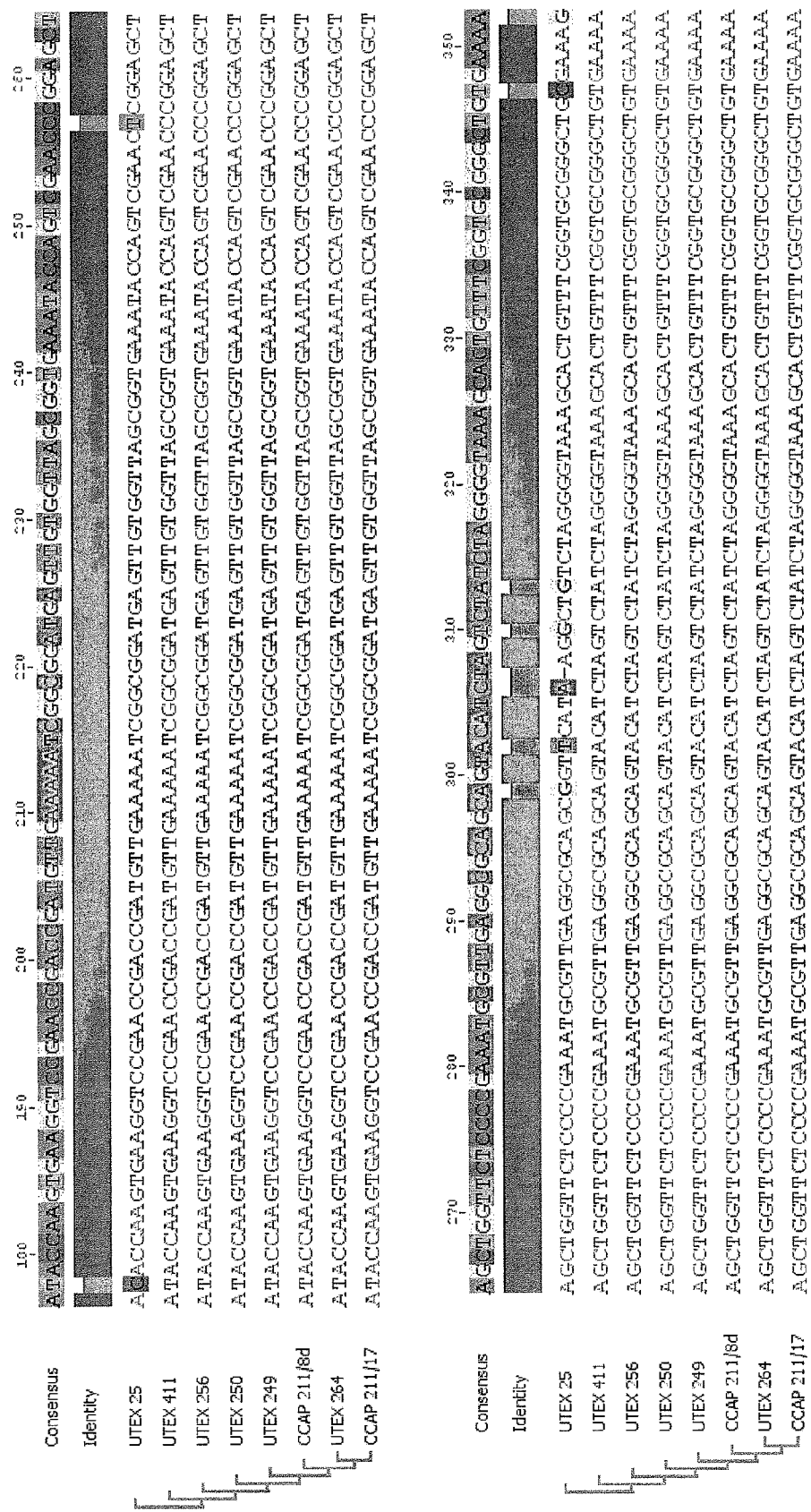
Figure 7C:
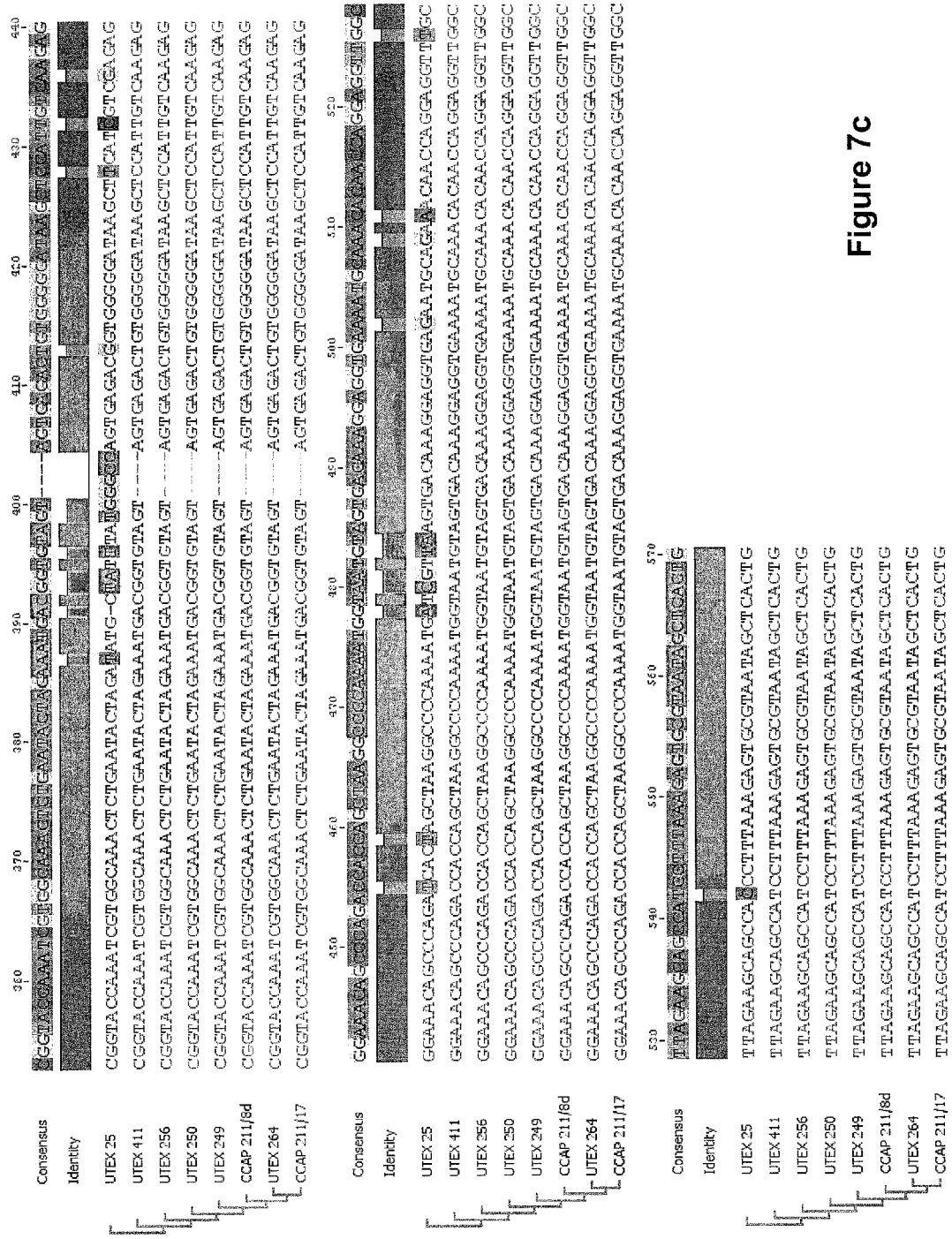

Five µl of total DNA, prepared as described above, from each *Chlorella protothecoides* strain, was diluted 1:50 in 10 mM Tris, pH 8.0. PCR reactions, final volume 20 µl, were set up as follows: Ten µl of 2× iProof HF master mix (Bio-Rad) was added to 0.4 µl primer SZ02613 (5'-TGTTGAAGAAT-GAGCCGGCGAC-3' (SEQ ID NO:3) at 10 mM stock concentration). This primer sequence runs from position 567-588 in GenBank accession no. L43357 and is highly conserved in higher plant and algal plastid genomes. This was followed by the addition of 0.4 µl primer SZ02615 (5'-CAGTGAGCTAT-TACGCACTC-3' (SEQ ID NO:4) at 10 mM stock concentration). This primer sequence is complementary to position 1112-1093 in GenBank accession no. L43357 and is highly conserved in higher plants and algal plastid genomes. Next, 5 µl of diluted total DNA and 3.2 µl dH$_2$O were added. PCR reactions were run as follows: 98° C., 45"; 98° C., 8"; 53° C., 12"; 72° C., 20" for 35 cycles followed by 72° C. for 1 minute and holding at 25° C. For purification of PCR products, 20 µl of 10 mM Tris, pH 8.0, was added to each reaction, followed by extraction with 40 µl of Phenol:Chloroform:Isoamyl alcohol (12:12:1), vortexing and centrifuging at 14,000×g for 5 minutes. PCR reactions were applied to S-400 columns (GE Healthcare) and centrifuged for 2 minutes at 3,000×g. Purified PCR products were subsequently TOPO coloned into PCR8/GW/TOPO and positive clones selected for on LB/Spec plates. Purified plasmid DNA was sequenced in both directions using M13 forward and reverse primers. Sequence alignments and results are summarized in Cladograms in FIGS. 7a-7c. Sequences from all eight strains of *Chlorella protothecoides* are listed as SEQ ID NO:5 and SEQ ID NO:6 in the attached Sequence Listing.

---

What is claimed is:

1. A method of treating a patient having a condition related to impaired glucose metabolism, comprising determining the patient has impaired glucose metabolism and administering to the patient an effective regime of microalgal biomass comprising at least 15% algal oil by dry weight, wherein the microalgal biomass is derived from *Chlorella protothecoides* and the regime lowers the percentage fat of total body weight in the patient relative to the percentage before the administering step.

2. The method of claim 1, wherein the microalgal biomass contains 25-75% of algal oil by dry weight.

3. The method of claim 1, wherein at least 50% by weight of the algal oil is monounsaturated oil.

4. The method of claim 1, wherein less than 5% by weight of the algal oil is docosahexanoic acid (DHA).

5. The method of claim 1, wherein the algal oil is predominantly encapsulated in cells of the microalgal biomass.

6. The method of claim 1, wherein the microalgal biomass is administered as a homogenate.

7. The method of claim 1, wherein the patient has a condition selected from the group consisting of impaired glucose tolerance, impaired fasting glucose, and/or diabetes.

8. The method of claim 1, wherein the regime comprises administering the microalgal biomass at a dose of 1-20% of food by weight or calories.

9. The method of claim 1, wherein the microalgal biomass is administered daily for at least a week.

10. The method of claim 1, wherein the microalgal biomass is administered with at least one other edible ingredient as a food composition.

11. The method of claim 1, wherein the patient receives an alternative treatment for impaired glucose metabolism before the administering step and the alternative treatment is reduced or eliminated after the administering step.

12. The method of claim 1, further comprising monitoring blood glucose levels of the patient, wherein the regime lowers the mean plasma glucose concentration of the patient relative to the concentration before the administering step.

13. The method of claim 1, wherein the algal biomass is derived from *Chlorella protothecoides* grown heterotrophically.

14. The method of claim 13, wherein the *Chlorella protothecoides* is grown in a culture medium including a feedstock comprising at least one carbon substrate selected from the group consisting of a depolymerized cellulosic material, a 5-carbon sugar, and a 6-carbon sugar.

15. The method of claim 1, wherein the microalgal biomass is administered in the form of a tablet or capsule.

16. The method of claim 1, wherein the microalgal biomass is administered in the form of a food product.

17. The method of claim 1, wherein treating the patient comprises reducing the patient's mean blood glucose level relative to the level before administering the regime.

* * * * *

UNITED STATES PATENT AND TRADEMARK OFFICE
CERTIFICATE OF CORRECTION

| | | |
|---|---|---|
| PATENT NO. | : 8,747,834 B2 | Page 1 of 1 |
| APPLICATION NO. | : 13/254035 | |
| DATED | : June 10, 2014 | |
| INVENTOR(S) | : David Brinkmann et al. | |

It is certified that error appears in the above-identified patent and that said Letters Patent is hereby corrected as shown below:

In the Claims

In Claim 13, Column 42, line 20, delete "algal blomass"

and replace it with --microalgal biomass--.

Signed and Sealed this
Eleventh Day of November, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagagtttg atcatggctc ag                                                  22

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
ctgctgcctc ccgtag                                                      16

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgttgaagaa tgagccggcg ac                                               22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtgagcta ttacgcactc                                                  20

<210> SEQ ID NO 5
<211> LENGTH: 546
<212> TYPE: DNA
<213> ORGANISM: Chlorella protothecoides

<400> SEQUENCE: 5
tgttgaagaa tgagccggcg acttagaaaa cgtggcaagg ttaaggaaac gtatccggag      60
ccgaagcgaa agcaagtctg aacagggcga ttaagtcatt ttttctagac ccgaacccgg     120
gtgatctaac catgaccagg atgaagcttg ggtgacacca agtgaaggtc cgaaccgacc     180
gatgttgaaa atcggcgga tgagttgtgg ttagcggtga ataccagtc gaactcggag       240 ctagctggtt ctccccgaaa tgcgttgagg cgcagcggtt cataaggctg tctagggta     300 aagcactgtt tcggtgcggg ctgcgaaagc ggtaccaaat cgtggcaaac tctgaatact     360
agatatgcta tttatgggcc agtgagacgg tgggggataa gcttcatcgt cgagagggaa    420
acagcccaga tcactagcta aggccccaaa atgatcgtta agtgacaaag gaggtgagaa    480
tgcagaaaca accaggaggt ttgcttagaa gcagccaccc tttaaagagt gcgtaatagc    540
tcactg                                                                546

<210> SEQ ID NO 6
<211> LENGTH: 565
<212> TYPE: DNA
<213> ORGANISM: Chlorella protothecoides

<400> SEQUENCE: 6
tgttgaagaa tgagccggcg acttagaaaa agtggcgtgg ttaaggaaaa attccgaagc     60
cttagcgaaa gcgagtctga atagggcgat caaatatttt aatatttaca atttagtcat    120
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaaa acggtaccaa    360
atcgtggcaa actctgaata ctagaaatga cggtgtagta gtgagactgt gggggataag    420
ctccattgtc aagagggaaa cagcccagac caccagctaa ggccccaaaa tggtaatgta    480

```
gtgacaaagg aggtgaaaat gcaaacacaa ccaggaggtt ggcttagaag cagccatcct    540
ttaaagagtg cgtaatagct cactg                                         565
```